US008772258B2

(12) United States Patent
Kirkpatrick et al.

(10) Patent No.: US 8,772,258 B2
(45) Date of Patent: Jul. 8, 2014

(54) SINGLE WALLED CARBON NANOTUBE/SIRNA COMPLEXES AND METHODS RELATED THERETO

(75) Inventors: D. Lynn Kirkpatrick, Houston, TX (US); Michelle K. Weiss, Houston, TX (US)

(73) Assignee: Ensysce Biosciences, Inc., Houston, TX (US)

( * ) Notice: Subject to any disclaimer, the term of this patent is extended or adjusted under 35 U.S.C. 154(b) by 0 days.

(21) Appl. No.: 13/175,314

(22) Filed: Jul. 1, 2011

(65) Prior Publication Data

US 2012/0003278 A1  Jan. 5, 2012

Related U.S. Application Data

(60) Provisional application No. 61/360,942, filed on Jul. 2, 2010.

(51) Int. Cl.
*C12N 15/113* (2010.01)
*C07H 21/02* (2006.01)

(52) U.S. Cl.
CPC .................................. *C12N 15/113* (2013.01)
USPC ....................................... 514/44 A; 536/24.5

(58) Field of Classification Search
None
See application file for complete search history.

(56) References Cited

U.S. PATENT DOCUMENTS

2006/0275371 A1  12/2006  Dai et al.
2011/0045080 A1  2/2011  Powis et al.

FOREIGN PATENT DOCUMENTS

WO    WO 2008/102728 A1    8/2008

OTHER PUBLICATIONS

Huczko, et al., Carbon Nanotubes: Experimental Evidence for a Null Risk of Skin Irritation and Allergy, *Fullerene Science and Technology*, (2001), 9(2):247-250.
Tasis, et al., Soluble Carbon Nanotubes, *Chemistry—A European Journal*, (Sep. 5, 2003), 9(17):4000-4008.
Lam, et al., Pulmonary Toxicity of Single-Wall Carbon Nanotubes in Mice 7 and 90 Days After Intratracheal Instillation, *Toxicological Sciences*, (published online Sep. 26, 2003), 77(1):126-134.
Warheit, et al., Comparative Pulmonary Toxicity Assessment of Single-Wall Carbon Nanotubes in Rats, *Toxicological Sciences*, (published online Sep. 26, 2003), 77(1):117-125.
Maynard, et al., Exposure to Carbon Nanotube Material: Aerosol Release During the Handling of Unrefined Single-Walled Carbon Nanotube Material, *Journal of Toxicology and Environmental Health, Part A*, (Jan. 2004), 67(1):87-107.
Pantarotto, et al., Functionalized Carbon Nanotubes for Plasmid DNA Gene Delivery, *Angewandte Chemie International Edition*, (published online Sep. 26, 2003), 43(39):5242-5246.
Huczko, et al., Pulmonary Toxicity of 1-D Nanocarbon Materials, *Fullerenes, Nanotubes and Carbon Nanostructures*, (2005), 13(2):141-145.
Yokoyama, et al., Biological Behavior of Hat-Stacked Carbon Nanofibers in the Subcutaneous Tissue in Rats, *Nano Letters*, (published online Dec. 8, 2004), 5(1):157-161.
Sato, et al., Influence of Length on Cytotoxicity of Multi-Walled Carbon Nanotubes Against Human Acute Monocytic Leukemia Cell Line THP-1 in vitro and Subcutaneous Tissue of Rats in vivo, *Molecular BioSystems*, (published online Apr. 20, 2005), 1(2):176-182.
Shvedova, et al., Unusual Inflammatory and Fibrogenic Pulmonary Responses to Single-Walled Carbon Nanotubes in Mice, *Am. J. of Physiology—Lung Cellular and Molecular Physiology*, (published online Jun. 2005), 289(5):L698-L708.
Lam, et al., A Review of Carbon Nanotube Toxicity and Assessment of Potential Occupational and Environmental Health Risks, *Critical Reviews in Toxicology*, (Jan. 2006) 36(3):189-217.
Sayes, et al., Functionalization Density Dependence of Single-Walled Carbon Nanotubes Cytotoxicity In Vitro, *Toxicology Letters*, (published online Oct. 17, 2005), 161(2):135-142.
Yang., et al., Single-Walled Carbon Nanotubes-Mediated in vivo and in vitro Delivery of siRNA Into Antigen-Presenting Cells, *Gene Therapy*, (published online Jul. 6, 2006), 13(24):1714-1723.
Singh, et al., Tissue Biodistribution and Blood Clearance Rates of Intravenously Administered Carbon Nanotube Radiotracers, *PNAS*, (published online Feb. 21, 2006), 103(9):3357-3362.
Cherukuri, et al., Mammalian Pharmacokinetics of Carbon Nanotubes Using Intrinsic Near-Infrared Fluorescence, *PNAS*, (Dec. 12, 2006), 103(50):18882-18886.
Yang, et al., Biodistribution of Pristine Single-Walled Carbon Nanotubes In Vivo, *J. Phys. Chem. C*, (published online Jun. 17, 2007), 111(48):17761-17764.
Ke, et al. Carbon Nanomaterials in Biological Systems, *J. Phys.: Condens. Matter*, (published online Jul. 27, 2007), 19(37):1-25.
Lacerda, et al., Tissue Histology and Physiology Following Intravenous Administration of Different Types of Functionalized Multiwalled Carbon Nanotubes, *Nanomedicine*, (Apr. 2008), 3(2):149-161.
Liu, et al., Circulation and Long-Term Fate of Functionalized, Biocompatible Single-Walled Carbon Nanotubes in Mice Probed by Raman Spectroscopy, *PNAS*, (published online Jan. 29, 2008), 105(5):1410-1415.
Schipper, et al., A Pilot Toxicology Study of Single-Walled Carbon Nanotubes in a Small Sample of Mice, *Nature Nanotechnology*, (published online Mar. 30, 2008), 3(4):216-221.
Kostarelos, The Long and Short of Carbon Nanotube Toxicity, *Nature Biotechnology*, (Jul. 2008), 26(7):774-776.
Liu, et al., Drug Delivery with Carbon Nanotubes for In Vivo Cancer Treatment, *Cancer Research*, (Aug. 15, 2008), 68(16):6652-6660.

(Continued)

*Primary Examiner* — Tracy Vivlemore
(74) *Attorney, Agent, or Firm* — Pepper Hamilton LLP

(57) ABSTRACT

The present invention includes single-walled carbon nanotube compositions for the delivery of bioactive agents and methods of making such single-walled carbon nanotube compositions.

12 Claims, 30 Drawing Sheets

(56) References Cited

OTHER PUBLICATIONS

Liu, et al., Supramolecular Stacking of Doxorubicin on Carbon Nanotubes for in vivo Cancer Therapy, *Angewwandte Chemie International Edition*, (published online Sep. 16, 2009), 48(41):7668-7672.

Bartholomeusz, et al., In vivo Therapeutic Silencing of Hypoxia-Inducible Factor 1 Alpha (HIF-1α) Using Single-Walled Carbon Nanotubes Noncovalently Coated with siRNA, *Nano Research*, (Apr. 2009), 2(4):279-291.

Liu, et al., Carbon Nanotubes in Biology and Medicine: In vitro and in vivo Detection, Imaging and Drug Delivery, *Nano Research*, (Feb. 2009), 2(2):85-120.

Pastorin, Crucial Functionalizations of Carbon Nanotubes for Improved Drug Delivery: A Valuable Option?, *Pharmaceutical Research*, (Apr. 2009), 26(4):746-769.

Kostarelos, et al., Promises, Facts and Challenges for Carbon Nanotubes in Imaging and Therapeutics, *Nature Nanotechnology*, (published online Sep. 27, 2009), 4(10):627-633.

Ruggiero, et al., Paradoxical Glomerular Filtration of Carbon Nanotubes, *PNAS*, (Jul. 6, 2010), 107(27):12369-12374.

Ruggiero, et al., Imaging and Treating Tumor Vasculature with Targeted Radiolabeled Carbon Nanotubes, *Int J of Nanomedicine*, (published online Oct. 5, 2010), 5:783-802.

Beg, et al., Advancement in Carbon Nanotubes: Basics, Biomedical Applications and Toxicity, *Journal of Pharmacy and Pharmacology*, (Feb. 2011), 63(2):141-163.

Han, et al., Effect of Hydrophilicity of Carbon Nanotube Arrays on the Release Rate and Activity of Recombinant Human Bone Morphogenetic Protein-2, *Nanotechnology*, (published online Jun. 21, 2011), 22(29):295712 (8 pp.).

International Search Report and Written Opinion from PCT/US2011/042832 dated Nov. 15, 2011.

A

B

A

B

SINGLE WALLED CARBON NANOTUBE/SIRNA COMPLEXES AND METHODS RELATED THERETO

CROSS-REFERENCE TO RELATED APPLICATIONS

This application claims priority to U.S. Provisional Application No. 61/360,942 entitled "Single-Walled Carbon Nanotube/SIRNA Complexes and Methods Related Thereto" filed Jul. 2, 2010, which is herein incorporated by reference in its entirety.

GOVERNMENT INTERESTS

Not applicable

PARTIES TO A JOINT RESEARCH AGREEMENT

This application includes subject matter that was made by or on behalf of Ensysce Biosciences, Inc. as a result of activities undertaken within the scope of joint research agreements between Ensysce Biosciences, Inc. and The University of Texas M.D. Anderson Cancer Center and Ensysce Biosciences, Inc. and William Marsh Rice University, that were in effect on or before the date such inventions were made.

INCORPORATION BY REFERENCE OF MATERIAL SUBMITTED ON A COMPACT DISC

Not applicable

BACKGROUND

Not applicable

SUMMARY

Some embodiments herein are directed to a pharmaceutical composition comprising an effective amount of one or more short-interfering ribonucleic acid (siRNA) complexed to single-walled carbon nanotubes; and a pharmaceutically acceptable excipient. In some embodiments, the single-walled carbon nanotubes may be unagglomerated and non-aggregated. In some embodiments, the single-walled carbon nanotubes have a diameter about 1 nm to about 2 nm. In some embodiments, the single-walled carbon nanotubes have an average length of about 600 nm or less, from about 100 nm to about 600 nm, about 400 nm, about 200 nm, from about 25 nm to about 250 nm, or a range between any two of these values. In some embodiments, the effective amount comprises up to about 100 mg, up to about 75 mg, up to about 50 mg, up to about 40 mg, up to about 30 mg, from about 15 mg to about 100 mg, from about 15 mg to about 75 mg, from about 15 mg to about 50 mg, from about 15 mg to about 40 mg, or from about 15 mg to about 30 mg of the one or more short-interfering ribonucleic acid (siRNA) complexed to single-walled carbon nanotubes. In some embodiments, the effective amount of one or more short-interfering ribonucleic acid (siRNA) is non-covalently complexed to single-walled carbon nanotubes.

In some embodiments, the short-interfering ribonucleic acid (siRNA) is targeted to messenger ribonucleic acid (mRNA) transcribed from genes selected from the group consisting of hypoxia-inducible factor 1 alpha (HIF-1α), thioredoxin (Trx), vascular endothelial growth factor (VEGF) mRNA, epidermal growth factor (EGFR), human epidermal growth factor receptor 2 (HER2), polo-like kinase 1 (PLK1), and kinase family member 11 (Kif11), epidermal growth factor receptors (EGFR, ErbB-1, HER1), and V-Ki-ras2 Kirsten rat sarcoma viral oncogene homolog (KRAS). In some embodiments, the pharmaceutically acceptable excipient is selected from water, saline, PLURONIC, polyethylene glycol (PEG), PEG-5000, PEG-5000 PE, PL-PEG (1,2-dimyristoyl-sn-glycero-3-phosphoethanolamine-N-[methoxy(polyethylene glycol)-5000] (ammonium salt), C18-PMH-mPEG (poly(maleic anhydride-alt-1-octadecene)-poly (ethylene glycol)methyl ether), and combinations thereof.

Some embodiments described herein are directed to a method for delivering siRNA to tumorigenic tissue comprising administering to a subject having tumorigenic tissue a pharmaceutical composition comprising an effective amount of one or more short-interfering ribonucleic acid (siRNA) complexed to single-walled carbon nanotubes; and a pharmaceutically acceptable excipient. In some embodiments, administering comprises intravenous injection. In some embodiments, the subject is selected from a mammal, a mouse, and a human. In some embodiments, the subject is a human having cancer. In some embodiments, the effective amount comprises up to about 100 mg, up to about 75 mg, up to about 50 mg, up to about 40 mg, up to about 30 mg, from about 15 mg to about 100 mg, from about 15 mg to about 75 mg, from about 15 mg to about 50 mg, from about 15 mg to about 40 mg, or from about 15 mg to about 30 mg of the one or more short-interfering ribonucleic acid (siRNA) complexed to single-walled carbon nanotubes. In some embodiments, a substantial portion of the one or more short-interfering ribonucleic acid (siRNA) complexed to single-walled carbon nanotubes accumulates in the tumorigenic tissue at sufficient concentrations to inhibit expression of at least one target associated with the one or more short-interfering ribonucleic acid (siRNA) tissue within about 1 hour after administration In some embodiments, substantially none of the one or more short-interfering ribonucleic acid (siRNA) complexed to single-walled carbon nanotubes are in circulation from about 5 to about 15 minutes after administration of the one or more short-interfering ribonucleic acid (siRNA) complexed to single-walled carbon nanotubes. In some embodiments, the effective amount of one or more short-interfering ribonucleic acid (siRNA) is non-covalently complexed to single-walled carbon nanotubes.

Some embodiments herein are directed to a method for inhibiting expression of a gene in a subject comprising administering to the subject a pharmaceutical composition comprising an effective amount of one or more short-interfering ribonucleic acid (siRNA) complexed to single-walled carbon nanotubes; and a pharmaceutically acceptable excipient.

Some embodiments may be directed to a pharmaceutical composition comprising an effective amount of one or more short-interfering ribonucleic acid (siRNA) complexed to carbon nanotubes; and a pharmaceutically acceptable excipient.

Some embodiments may be directed to a method for delivering siRNA to tumorigenic tissue comprising administering to a subject having tumorigenic tissue a pharmaceutical composition comprising an effective amount of one or more short-interfering ribonucleic acid (siRNA) complexed to carbon nanotubes; and a pharmaceutically acceptable excipient.

DESCRIPTION OF THE DRAWINGS

For a fuller understanding of the nature and advantages of the present invention, reference should be had to the following detailed description taken in connection with the accompanying drawings, in which:

FIG. 1C is a normalized emission spectra (using 658 nm excitation) of SWCNT solubilized with siRNA;

FIG. 4A shows the inhibition of HIF-1α activity in cells treated with the SWCNT-siHIF-1α complex as determined by luciferase assay, and FIG. 4B graphically depicts the inhibition of HIF-1α protein expression by Western blotting.

FIG. 6A graphically depicts the cell viability of MiaPaCa-HRE pancreatic cancer cells after delivery of a range of concentrations of toxic SWCNT/siRNA complexes. FIGS. 6B and 6C are images of HIF-1α activity in tumor bearing mice prior to addition of luciferin or 5 min after. FIG. 6D graphically depicts decreased tumor HIF-1α activity in mice given intratumoral injections of either siRNA targeting HIF-1α alone (siHIF-1α), a non-targeting siRNA complexed to SWCNT (SWCNT/siSc), or siRNA targeting HIF-1α complexed to SWCNT (SWCNT-siHIF) twice per week for 3 weeks. The mice treated with SWCNT/HIF complexes were compared to mice treated with complexes comprising either the control SWCNT/siRNA ($p<0.01$ to $p<0.05$) or HIF-1α siRNA alone, and FIG. 6E graphically depicts tumor volume as a function of days after cell injection of SWCNT/siRNA complexes.

FIG. 14A shows a time course of thioredoxin expression, and FIG. 14B shows thioredoxin expression as a result of incubation with increasing concentrations of SWCNT/(Trx)siRNA.

FIG. 15B shows a fluorometric analysis of a dispersion of the SWCNT/(Trx)siRNA, SWCNT/(EGFR)siRNA, and SWCNT/(Trx)siRNA/(EGFR)siRNA dual payload SWCNT used in FIG. 15A.

FIG. 26B shows a bar graph showing the percent control of thioredoxin expression in these tumors based on the Western blot of FIG. 26A.

FIG. 27B shows a bar graph showing the percent control of thioredoxin expression in these tumors based on the Western blot of FIG. 27A.

DETAILED DESCRIPTION

Figure 1:
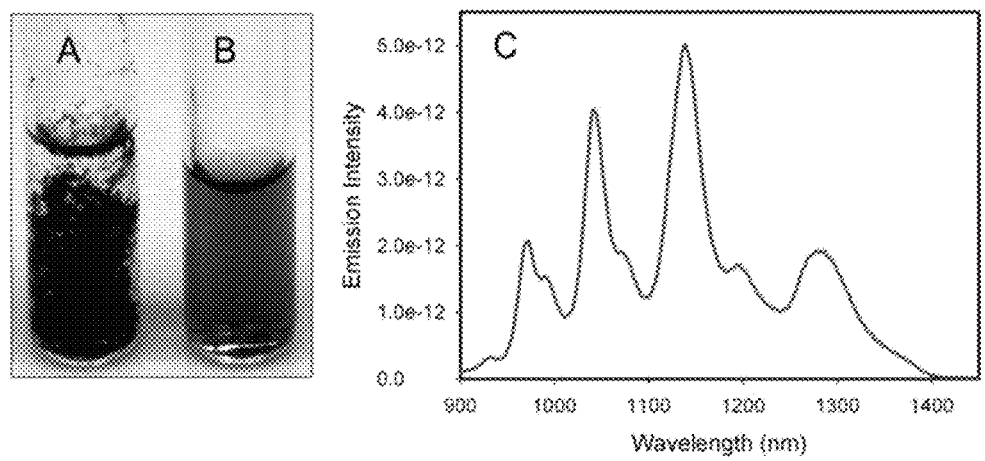
FIG. 1 shows single-walled carbon nanotubes (SWCNT) in solvent (FIG. 1A), and siRNA-solubilized SWCNT in solution (FIG. 1B).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must be noted that, as used herein, and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

The term "agglomeration," as used herein, refers to the formation of a cohesive mass of subunits such as carbon nanotubes held together by relatively weak forces such as, for example, van der Waals forces or capillary action, that can be broken during processing resulting in a group of individual subunits. The mass of subunits resulting from agglomeration is an "agglomerate."

As used herein, the term "aggregation" refers to the formation of a discrete group of subunits such as carbon nanotubes in which the forces holding the individual subunits together are not easily broken. For example, carbon nanotubes bundles can be strongly bonded together by, for example, covalent bonds. The discrete group of subunits is called an "aggregate."

As used herein, the term "bioactive substance" refers to a compound utilized to image, impact, treat, combat, ameliorate, prevent or improve an unwanted condition or disease of a patient. The bioactive substance may modulate any number of biological functions in the cell, such as cell division, cellular infection, cellular expression of cell surface proteins, cellular response to a hormone, among others. The term "bioactive substance" may further refer to polynucleotides, small molecules, and polypeptides that cause a metabolic change in a cell, generally by increasing transcription, expression or translocation of one or more genes, or by binding to an expressed protein.

The term "carbon nanotube" refers to an allotrope of carbon having a cylindrical or tube shape and a diameter of as small as about 1 nm. The term "carbon nanotube" may further include structures that can include, for example, metals, small-gap semiconductors, or large-gap semiconductors such as boron carbon nitride (BCN) nanotubes. The term carbon nanotube as used herein refers to both single-walled carbon nanotubes (SWCNT) and multi-walled carbon nanotubes (MWCNTs). A "single-walled carbon nanotube" or "SWCNT" refers to a carbon nanotube that consists of a one atom thick graphene sheet that has been rolled into a tube, A "multi-walled carbon nanotube" or "MWCNT" refers to a nanotube that include 2 or more one graphene sheets rolled into concentric tubes. The term "carbon nanotubes" may also be graphene in other forms including, for example, graphene spheres or "carbon nanosphere," which are commonly referred to as buckyballs or fullerene.

The term "diseased tissue", as used herein, refers to tissue or cells exhibiting a phenotype that is inconsistent with healthy tissue. For example, "diseased tissue" can include tissues and cells affected by AIDS; pathogen-borne diseases, which can be bacterial, viral, parasitic, or fungal, examples of pathogen-borne diseases include HIV, tuberculosis and malaria; hormone-related diseases, such as obesity; vascular system diseases; central nervous system diseases, such as multiple sclerosis; and undesirable matter, such as adverse angiogenesis, restenosis amyloidosis, toxins, reaction-by-products associated with organ transplants, and other abnormal cell or tissue growth. In some embodiments, "diseased tissue" can refer to tissues and cells associated with solid tumors or other cancerous growth including, but not limited to, those associated with bone, lung, vascular, neuronal, colon, ovarian, breast, and prostate cancer. The term diseased tissue may also refer to tissue or cells of the immune system, such as tissue or cells An "effective amount" or "therapeutically effective amount" of a composition, as used herein, refers to an amount of a biologically active molecule or complex or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like.

"Gene silencing" as used herein can refer to the suppression of gene expression from, for example, an endogenous gene, exogenous gene, or a transgene, and heterologous gene. Gene silencing may be mediated through processes that affect transcription, through post-transcriptional processing of RNA transcripts, and/or translation of the RNA transcript. In some embodiments, gene silencing can occur through siRNA mediated degradation of mRNA via RNA interference.

The term "knock-down" refers to gene silencing in which the expression of a target gene is reduced as compared with normal gene expression, but gene expression not completely eliminated. Knocking down gene expression can lead to the inhibition of production of the target gene product.

The term "non-functionalized," as used herein, refers to a chemical composition such as, a carbon nanotube, that are substantially unmodified. As such, each carbon of the carbon nanotube is covalently bonded to a neighboring carbon atom or an unreactive atom such as, for example, hydrogen. Non-functionalized carbon nanotubes do not include reactive functional groups, i.e., a group of atoms capable of forming a covalent bond to a carbon atom or another functional group, covalently bonded to the carbons of the carbon nanotube.

The term "nucleic acid" refers to chemical compositions of monomers having a sugar moiety, a phosphate, and a purine or pyrimidine base and includes deoxyribonucleic acids and ribonucleic acids as well as any single-stranded or double-stranded polymers thereof. Unless specifically limited, the term "nucleic acid" further encompasses known analogs of natural nucleotides that may have similar binding properties with reference to the naturally occurring nucleic acid analog and may be metabolized in a manner similar to naturally occurring nucleotides. Polymeric nucleic acids are generally referred to as "DNA" when the individual monomers making up the polymeric nucleic acid are deoxyribonucleic acids and "RNA" when the individual monomers making up the polymeric nucleic acid are ribonucleic acids. However, polymeric nucleic acids can include hybrid molecules that can include both deoxyribonucleic acid and ribonucleic acid monomers. Such polymeric nucleic acids may be arranged in any manner. For example, a polymeric nucleic acid may include complementary sequences that allow intermolecular interactions such that the polymeric nucleic acid to include secondary structural elements, or two single stranded polymeric nucleic acid molecules may include complementary sequences that allow intramolecular interactions such that the individual polymeric nucleic acids may bind to one another creating a double stranded polymeric nucleic acid molecule.

The arrangement of nucleic acid monomers in a particular polymeric nucleic acid molecule is commonly referred to as the "sequence" of that nucleic acid molecule. In a phenomenon referred to as "base pairing" a purine nucleic acid monomers, adenine (A) and guanine (G) form hydrogen bonds selectively with pyrimidine nucleic acid monomers thymine (T) and cytosine (C), respectively, to create A-T and G-C "base pairs." Ribonucleic acids are capable of forming similar base pairs; however, thyamine (T) is replaced with uracil (U) to create a A-U base pair. For DNA and messenger RNA (mRNA), RNA molecules produced as the result of transcription that have a sequence that is complementary to the DNA molecule from which the mRNA is produced, the nucleic acid monomers of a sequence may be arranged in three base pair "codons," where each codon of the mRNA corresponds to a specific amino acid that transported from the cytosol to a ribosome via transfer RNA (tRNA) during translation.

By "complementary sequence" is meant that the polymeric nucleic acid molecule includes a sequence of individual monomers that allow hydrogen bonds to form between nucleic acid monomers. A "complementary sequence" encompasses a pair of nucleic acid molecules in which each base pair is exactly complementary to the corresponding base pair to the opposing nucleic acid. "Complementary sequence" also encompasses a pair of nucleic acid molecules in which one of the pair include conservatively modified variants of naturally occurring nucleotides and degenerate codon substitutions. For example, degenerate codon substitutions may be achieved by generating sequences in which the third position of one or more selected (or all) codons is substituted with mixed-base and/or deoxyinosine residues.

The term "subject" or "patient," as used herein, includes human and non-human vertebrates such as wild, domestic, and farm animals.

As used herein, a "pharmaceutically acceptable carrier" is a pharmaceutically acceptable solvent, suspending agent or vehicle for delivering the complexes of the present invention to the patient. The carrier may be liquid or solid and is selected with the planned manner of administration in mind. Examples of pharmaceutically acceptable carriers that may be utilized in accordance with the present invention include, but are not limited to, water, isotonic salt solution, isotonic sugar solution, polyethylene glycol (PEG), aqueous PEG solutions, liposomes, ethanol, organic solvent (e.g. DMSO) dissolved in isotonic aqueous solution, aqueous buffers, oils, and combinations thereof.

The terms "small interfering RNA," "short interfering RNA," or "siRNA" refers to short double stranded RNA molecules in which one strand of the double stranded RNA is complementary to a portion of a target gene. An "RNA duplex" or "double-stranded RNA" refers to the structure formed by the complementary pairing between two regions of a RNA molecule. In some embodiments, the length of an siRNA molecule may be less than about 30 nucleotides. For example, the siRNA can be 29, 28, 27, 26, 25, 24, 23, 22, 21, 20, 19, 18, 17, 16, 15, 14, 13, 12, 11 or 10 nucleotides in length, and in particular embodiments, the length of the duplex may be 19 to 25 nucleotides in length. In some embodiments, siRNA may consist of two complementary RNA molecules that are held together by the hydrogen bonding between base pairs, and in some embodiments, the siRNA may include a 3' or a 5' overhang of 1, 2, 3, 4 or 5 nucleotides on either end of the siRNA molecule. In other embodiments, the RNA duplex portion of the siRNA can be part of a hairpin structure prepared from a long single strand of RNA that includes at least two complementary sequences. siRNA including such a hairpin structure are sometime referred to as short hairpin RNA or (shRNA). In such embodiments, a loop can be formed between the two sequences that form the duplex. The loop can vary in length. For example, in some embodiments the loop may be 5, 6, 7, 8, 9, 10, 11, 12 or 13 nucleotides in length. In other embodiments, the hairpin structure can include 3' or 5' overhang portions.

The siRNA described herein includes double-stranded RNA molecules that are prepared from unmodified, naturally occurring RNA bases as well as siRNA that, for example, include non-naturally occurring RNA base pairs or are chemically-modified siRNA or otherwise stabilized siRNA. siRNA can also include siRNA that are specifically designed to target a specific gene, "targeting siRNA," and siRNA having a randomly generated sequence, "non-targeting siRNA."

"RNA interference (RNAi)" is the process of sequence-specific, posttranscriptional gene silencing initiated by siRNA. RNAi is seen in a number of organisms such as *Drosophila*, nematodes, fungi and plants and is believed to be involved in anti-viral defense, modulation of transposon activity, and regulation of gene expression. During RNAi, siRNA induces degradation of target mRNA and consequently inhibition of gene expression.

Various embodiments described herein are directed carbon nanotubes, and in some embodiments, single-walled carbon nanotubes (SWCNT), that are useful for delivery of a bioactive agent. In such embodiments, the bioactive agent may coat the carbon nanotube or SWCNT by forming covalent or non-covalent interactions with the carbon nanotube or SWCNT. In certain embodiments, bioactive agent coated carbon nanotube or SWCNT may be combined in a pharmaceutical composition that can be administered to a subject to facilitate delivery of the bioactive agent to the subject. Accordingly, some embodiments described herein include pharmaceutical compositions at least including bioactive agent coated carbon nanotube or SWCNT and a pharmaceutically acceptable carrier, and other embodiments include methods for using such pharmaceutical compositions for treating a subject. While such embodiments are not limited to a particular treating a particular disease, in certain embodiments, the disease may be cancer or another disease characterized by abnormal cell growth.

The carbon nanotube or SWCNT of various embodiments may be any carbon nanotube or single-walled carbon nanotubes known in the art. In some embodiments, the carbon nanotube or SWCNT may have a diameter for from about 0.5 nm to about 1.5 nm, and in other embodiments, the diameter may be about 1 nm. In still other embodiments, the length of the carbon nanotube or SWCNT may be about 300 nm or less. For example, in some embodiments, the carbon nanotube or SWCNT may have a length of from about 100 nm to about 400 nm, and in other embodiments, the carbon nanotube or SWCNT may have a length of about 150 nm to about 300 nm or about 175 nm to about 250 nm. Near-infrared spectral analysis provides a means for determining nanotube size distribution, purity, concentration in solution, and individualization, and in certain embodiments, the carbon nanotube or SWCNT may have a strong near-IR spectral transition in, for example, a range of from about 850 nm to about 1600 nm.

The carbon nanotube or SWCNT of embodiments may be derived from any source. For example, in some embodiments, the carbon nanotube or SWCNT may be produced by known methods including, but not limited to, arc discharge, laser evaporation, chemical vapor deposition, and the like, and in other embodiments, as high quality inexpensive carbon nanotube or SWCNT can be prepared using known catalyst chemical vapor deposition methods. In certain embodiments, carbon nanotube or SWCNT may be prepared using the high pressure carbon-monoxide method (HiPco), in which high pressure carbon monoxide (CO) is disproportionated on iron (Fe) nanoparticles formed in the gas phase from iron pentacarbonyl $(Fe(CO)_5)$ decomposition. Without wishing to be bound by theory, the HiPCO method may produce relatively small diameter nanotubes.

Embodiments described herein are not limited to any particular bioactive agent. For example, in various embodiments, the bioactive agent may be a drugs, vaccines, immunological agents, chemotherapeutic agent, diagnostic agent, prophylactic agent, nutraceutical agent, small molecule, nucleic acid, protein, peptide, lipid, carbohydrate, hormone, and combinations thereof. In particular embodiments, the bioactive substance may be siRNA. The siRNA of such embodiments may be of any sequence and may be composed of naturally occurring or non-naturally occurring base pairs. In some embodiments, the siRNA may be double-stranded RNA, and in other embodiments, the siRNA may be hairpin siRNA. In still other embodiments, the siRNA unmodified, and in yet other, the siRNA may be chemically-modified. Embodiments are not limited to a particular sequence, and in some embodiments, the siRNA may include a sequence that allows the siRNA to specifically target a specific gene thereby inhibiting expression of that particular gene. In other embodiments, the siRNA may be of random sequence. In certain embodiments, the siRNA may be of a sequence that allows the siRNA to specifically target and inhibit the expression hypoxia-inducible factor 1 alpha (HIF-1α), polio-like kinase 1 (PLK1), kinase-like family 11 (Klf11), thioredoxin (Trx), epidermal growth factor receptors (EGFR, ErbB-1, HER1), V-Ki-ras2 Kirsten rat sarcoma viral oncogene homolog (KRAS), and the like.

In some embodiments, the SWCNT may be combined with a bioactive agent to make a SWCNT/bioactive agent complex, in which the bioactive agent forms a non-covalent association with the SWCNT, and in other embodiments, the SWCNT may be combined with a bioactive agent to make a SWCNT/bioactive agent complex, in which covalent bonds associate the bioactive agent with the SWCNT. In still other embodiments, the SWCNT may be combined with siRNA to make a SWCNT/siRNA complex, in which each delivery vehicle only includes a SWCNT and one or more siRNA molecule associated with the SWCNT. As used herein, the term "SWCNT complexes" shall encompass both SWCNT/bioactive agent complexes and, in particular, SWCNT/siRNA agent complexes. The amount of bioactive agent or siRNA combined with the SWCNT may vary among embodiments and may be determined based on the amount of surface of each SWCNT to be covered by active agent or siRNA. For example, in some embodiments, the ratio of complexed to non-complexed surface area on the SWCNT may be selected to provide sufficient coverage to allow the SWCNT to be soluble in solution and provide a therapeutically effective amount of bioactive agent to be delivered. In certain embodiments, less than about 95% of the total surface area of the SWCNT may be in complex with the bioactive active agent and/or solubilization agent, and in other embodiments, less than about 50% of the surface area of the SWCNT may be in complex with the bioactive agent and/or solubilization agent. The amounts of SWCNT and bioactive agent or siRNA combined to form the SWCNT complexes may, therefore, vary accordingly. For example in some embodiments, a composition of SWCNT complexes may include about 1 ng/μl to about 10 ng/μl based on the total volume of the composition and about 10 ng/μl to about 40 ng/μl of siRNA. In other embodiments, the SWCNT may be provided in a concentration of about 2 ng/μl to about 5 ng/μl and about 15 ng/μl to about 30 ng/μl of siRNA or about 3 ng/μl of SWCNT and about 25 ng/μl of siRNA. In some embodiments, the SWCNT/siRNA complex is administered in an effective amount. In some embodiments, an effective amount may comprise up to about 100 mg, up to about 75 mg, up to about 50 mg, up to about 40 mg, up to about 30 mg, from about 15 mg to about 100 mg, from about 15 mg to about 75 mg, from about 15 mg to about 50 mg, from about 15 mg to about 40 mg, or from about 15 mg to about 30 mg of the one or more short-interfering ribonucleic acid (siRNA) complexed to single-walled carbon nanotubes.

In other embodiments, the SWCNT/siRNA complex may further include one or more solubilization agent, and in some embodiments, the solubilization agent may be a mild detergent that can associate with the SWCNT/siRNA complex and allow improved the solubility of the SWCNT/siRNA complex. For example, in particular embodiments, the detergent may be a polyalkylene oxide such as, for example, PLURONIC™, PEG 5000, PEG5000 PE (1,2-dimyristoyl-sn-glycero-3-phosphoethanolamine-N-[methoxy(polyethylene glycol)-5000] (ammonium salt), C18-PMH-mPEG (poly (maleic anhydride-alt-1-octadecene)-poly(ethylene glycol) methyl ether), or a combination thereof. The concentration of the detergent may vary in embodiments and may be sufficient to increase solubilization without effecting the stability of the SWCNT complexes or the physiological acceptability of the compositions. For example, in some embodiments, the solubilization may be provided at about 1% to about 7% of the total solution, and in other embodiments, the detergent may be provided at about 2% to about 5% of the total solution. In particular embodiments, the detergent may be provided at about 3% of the solution.

In some embodiments, the SWCNT/bioactive agent complex or SWCNT/siRNA agent complex may be prepared in an aqueous buffer that is physiologically acceptable for in vivo or in vitro use, and in other embodiments, the SWCNT complexes may be prepared in a buffer suitable for administration to a mammal such as, for example, a mouse, rabbit, ape, or human. As such, in certain embodiments, the SWCNT complexes may be combined with one or more pharmaceutically acceptable carrier or excipient to produce a pharmaceutical formulation. The carrier or excipient may vary among embodiments and may be selected based on factors including, but not limited to, route of administration, location of the disease tissue, the bioactive substance being delivered, and/or time course of delivery of the bioactive substance. For example, in some embodiments, the pharmaceutically acceptable carrier may be water, and in other embodiments, the pharmaceutically acceptable carrier may be water combined with a physiologic salt to create an aqueous solution that is isotonic to blood serum. In still other embodiments, the pharmaceutical compositions of embodiments can include one or more preservative.

As above, in some embodiments, the pharmaceutical compositions may include a solubilization agent such as, but not limited to, polyalkylene oxides such as, for example, PLURONIC™, PEG, PEG-5000, PEG-5000 PE, PL-PEG (1,2-dimyristoyl-sn-glycero-3-phosphoethanolamine-N-[methoxy(polyethylene glycol)-5000] (ammonium salt), C18-PMH-mPEG (poly(maleic anhydride-alt-1-octadecene)-poly(ethylene glycol)methyl ether) or a combination thereof. In particular embodiments, at least about 50% or at least about 75% of the total SWCNT complexes in the composition may be solubilized in the pharmaceutically acceptable carrier solution by association of only siRNA. The addition of 1% to about 7% or about 2% to about 5% of the total solution of a solubilization agent may further increase the solubility of the SWCNT complexes such that up to about 85%, up to about 95%, or up to about 100% of the SWCNT complexes.

The pharmaceutical compositions of various embodiments may be prepared to deliver of a therapeutically effective amount of the bioactive agent to the subject. For example, in embodiments in which the bioactive agent is a siRNA, an effective amount of the SWCNT/siRNA complex may be an amount sufficient to reduce expression of the target gene in affected tissue. The effect of such reduced expression of the target gene may be evident based on physiological changes in the affected tissue such as, for example, reduced rate of cell proliferation in tumorigenic tissue, reduction or maintenance of tumor size, reduction or reversal of other symptoms associated with the disease, and combinations thereof. Reduced expression may be also, or alternatively, be evident by reduced expression of the target gene based on pre-administration expression levels in the patient or comparisons to administration of siRNA that is not complexed to SWCNT or vehicle controls. The therapeutically effective amount may vary depending on the type disease being treated, the extent of disease, disease progression, age of the patient, weight of the patient, and the like. In some embodiments, a therapeutically effective amount may be up to about 5 µg/kg or greater. In other embodiments, a therapeutically effective amount may be from about 0.1 µg/kg to about 4 µg/kg or greater, and in still other embodiments, a therapeutically effective amount may be from about 0.5 µg/kg to about 3 µg/kg or about 2.5 µg/kg.

Without wishing to be bound by theory, the SWCNT complexes of various embodiments may be very well tolerated when administered to a patient, such that large doses of a SWCNT complex may be provided to a patient with limited or no adverse side effects. For example, in some embodiments, a dose of greater than 10 mg or greater than 15 mg may be administered to a human without adverse side effects. Accordingly, various embodiments include pharmaceutical compositions prepared for high dose administration of SWCNT complexes.

Further embodiments are directed to methods for delivering a bioactive agent to diseased tissue including the steps of administering a therapeutically effective amount of a SWCNT complex to a patient, methods for treating a disease by administering a pharmaceutical composition including a therapeutically effective amount of a SWCNT complex to a patient in need of treatment, and methods for silencing a targeted gene in vivo including administering a therapeutically effective amount of a SWCNT complex to a patient. Any SWCNT complex including any bioactive agent described herein may be administered as part of a pharmaceutical composition in such methods. In certain embodiments, the SWCNT complex to be delivered may be a SWCNT/siRNA complex. In some embodiments, delivering may include contacting diseased tissue with the bioactive agent, and in some embodiments, delivering may include internalization of the active agent and, in certain embodiments, SWCNT into cells of the diseased tissue. For example, about 0.01% to about 30% of the total SWCNT/siRNA complex can be internalized the in vitro in media containing 10% serum after about 1 hour, from about 20% to about 90% of the total SWCNT/siRNA complex can internalized after about 3 hours, and after about 24 hours about 95% of more of the total SWCNT/siRNA complex can be internalized. The bioactive agent may remain in complex with the SWCNT after being internalized by the cell, or in some embodiments, the bioactive agent may dissociate from the SWCNT when internalized by the cell.

A broad range of diseases can be treated using the methods described herein, as SWCNT complexes of various embodiments can function as a serum-insensitive transfection agent to effectuate delivery of various bioactive agents into a cell. For example, in some embodiments, SWCNT/siRNA complex may be used to deliver siRNA to diseased tissues and cells to induce an RNAi response, which can effectively treat any disease in which aberrant gene expression leads to a diseased state. Moreover, because siRNA can silence target genes with a high degree of specificity, the SWCNT/siRNA complexes of various embodiments may be safely administered to treat nearly any disease for which an aberrantly expressed gene has been identified. For example, in particular exemplary embodiments, the siRNA of SWCNT/siRNA complexes may targeting HIF-1α expression. HIF-1α has been associated with a number of disease states including, but are not limited to, cancers such as, for example, breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, lymphoma, and blood cancer, angiogenic diseases such as, for example, diabetic retinopathy, age-related macular degeneration, and inflammatory diseases, inflammatory disease such as, for example, psoriasis and rheumatoid arthritis. Accordingly, in particular embodiments, SWCNT/siRNA complexes with siRNA targeting HIF-1α may be administered to treat any of these disease states.

The pharmaceutical compositions of described herein can be administered in any conventional manner by any route where they are active. Administration can be systemic or local. For example, administration can be, but is not limited to, parenteral, subcutaneous, intravenous, intramuscular, intraperitoneal, transdermal, oral, buccal, ocular, intravaginally, or inhalation. In certain embodiments, the administration may be systemic by intravenous injection, and in other embodiments, the administration to subjects exhibiting cancer may be by intratumoral injection. In some embodiments, the pharmaceutical composition may be prepared in the presence or absence of stabilizing additives that favors extended systemic uptake, tissue half-life, and intracellular delivery. Thus, modes of administration for the compounds of the present invention either alone or in combination with other pharmaceuticals can be injectable, including short-acting, depot, implant, and pellet forms injected subcutaneously or intramuscularly. In some embodiments, an injectable formulation including SWCNT complexes may be deposited to a site of the diseased tissue, such as, for example, in some embodiments, the pharmaceutical composition may be administered directly to tumorigenic tissue. In other embodiments, the pharmaceutical composition may be administered systemically by, for example, intravenous injection.

The frequency of administration may vary depending on the disease indication being treated and the patients response to the treatment. For example, in some embodiments, a pharmaceutical composition including SWCNT complexes may be administered at least once ever 12 hours, at least once every 24 hours, at least once every 48 hours, or at least once every 72 hours. Without wishing to be bound by theory, the half-life of the SWCNT complexes may be relatively short in circulation; however, despite this limited half-life in circulation, the SWCNT complexes may retain activity in affected tissue for at least about 24 hours following administration. For example, in some embodiments, a SWCNT/siRNA complex may be detectable in the blood stream of a patient to whom a pharmaceutical composition including a SWCNT/siRNA complex for up to about 30 minutes or up to about 15 minutes, but reduction in expression of a target gene may be observed for up to at least 12 hours or at least 24 hours. Thus, while the half-life of the SWCNT/siRNA complex may be relatively short, sufficient levels of siRNA can be delivered to affected tissue to adequately reduce target gene expression from a single therapeutically effect dose once every 12 hours or 24 hours. The frequency of administration of a pharmaceutical composition including a SWCNT/siRNA complex may, therefore, be reduced based on the effect rather than concentration of the SWCNT/siRNA complex in circulation.

The amount of SWCNT complexes in circulation following administration may be further effected by introduction of a solubilization agent into the pharmaceutical composition. For example, in some embodiments, the half-life of a pharmaceutical composition in circulation may be increased by providing SWCNT complexes having up to about a 10:1 ratio of a solubilization agent to the bioactive agent, and in other embodiments, the ratio of solubilization agent to bioactive agent in SWCNT complexes having extended half life may be from about 8:1 to about 1:1, or about 7:1. Without wishing to be bound by theory, SWCNT complex having a high ratio of solubilization agent to bioactive agent may exhibit a half-life in circulation of about 30 minutes or more, about 15 minutes or more, about 10 minutes or more, or about 5 minutes or more. In still other embodiments, the solubilization agent may be provided at less than a 1:1 ratio as compared to the bioactive agent. For example, in some embodiments, the ratio of solubilization agent to bioactive agent may be about 1:10, and in other embodiments, about 1:2 to about 1:8, or about 1:7. In embodiments with a low ratio of solubilization agent to bioactive agent, almost no SWCNT complexes may be detectable in circulation following administration; however, the reduced half-life for the SWCNT complexes in circulation may not effect of the pharmaceutical composition on the target tissue.

Yet further embodiments are directed to methods for preparing a SWCNT complexes including the steps of combining a bioactive agent in an aqueous solution with SWCNT and sonicating the SWCNT/bioactive agent solution. In some embodiments, the bioactive agent may be siRNA, and the concentration of siRNA in the aqueous solution, in such embodiments, may be up to about 100 µM, or in some embodiments, from about 5 µM to about 50 µM or about 10 µM to about 30 µM. In particular embodiments, the concentration of bioactive may be about 20 µM. In some embodiments, the SWCNT that are combined with the bioactive agent in the aqueous solution may be provided in an aqueous solution at a concentration of about 1 ppm to about 10 ppm or up to concentration of about 500 mg/mL, and when combined with the bioactive the concentration of SWCNT in the SWCNT/bioactive agent solution may be about 10 µg/mL to about 500 µg/mL or about 25 µg/mL to about 300 µg/mL. In some embodiments, the SWCNT/bioactive agent solution may further include one or more solubilization agents. For example, in certain embodiments, a solubilization agent may be added to the aqueous solution to provide a final concentration of solubilization agent of about 1% to about 7%, about 2% to about 5%, or about 3% of the total solution.

The aqueous solution of various embodiments may be any buffer known in the art that is useful during sonication and may include any number of chemical additives. For example, in some embodiments, the aqueous solution may be a buffer solution of about 100 mM KCl, 30 mM HEPES-KOH, and 1 mM $MgCl_2$ or 0.9% NaCl. The pH of such buffer solutions may be approximately neutral, for example, from about 6.5 to about 8.0. In particular embodiments, the aqueous solution may be suitable for in vivo administration of the SWCNT complexes. As such, in some embodiments, salt and pH concentrations may be within physiological ranges, and in other embodiments, the aqueous solution may be sterilized by known methods. The SWNCT complexes in the aqueous solution may, therefore, be administered immediately following sonication.

Sonication may be carried out using any sonication device known in the art, and the parameters for sonication may vary depending, for example, on the type of bioactive agent being associated with the SWCNT. For example, in embodiments in which siRNA is associated with SWCNT, the SWCNT/siRNA solution prepared as described above, which may or may not include a solubilization agent, may be sonicated in 15 second bursts with 45 second intervals between bursts. In some embodiments, the method for sonication may include two 15 second bursts each burst followed by a 45 second interval or sixteen 15 second bursts each followed by a 45 second interval. In particular embodiments, the temperature of the samples during sonication may be maintained at about 25° C. during the bursts, and the samples may be placed on ice during the 45 second intervals between bursts. The sonicator's settings during sonication may vary. For example, in some embodiments, the sonicator may be set to about 130 W, 20 kHz, and 40% amplitude.

The methods of some embodiments may further include the step of removing insoluble materials from the aqueous solution following sonication. The step of removing insoluble materials may be carried out by any means known in the art. For example, in some embodiments, insoluble materials may be removed by filtration, and in other embodiments, insoluble materials may be removed by centrifugation using parameters such as, 15,000×g for 5 minutes.

Various modifications of the invention, in addition to those described herein, will be apparent to those skilled in the art from the foregoing description. Such modifications are intended to fall within the scope of the appended claims.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples. The following examples are for illustrative purposes only and are not to be construed as limiting the invention in any manner.

Example 1

Preparation of Noncovalent Complexes of SWCNT with siRNA

SWCNT were produced using a high-pressure carbon monoxide (HiPco) process. The raw HiPco SWCNT product was added to an aqueous buffer solution (100 mM KCl, 30 mM HEPES-KOH [pH 7.5], 1 mM $MgCl_2$) containing 20 µM solubilized pooled siRNA [(siRNA targeting HIF-1α (HIF-1α) 5'-CCUGUGUCUAAAUCUGAAC-3', (SEQ ID 1), 5' CUACCUUCGUGAUUCUGUUU-3', (SEQ ID 2), GCACAAUAGACAGCGAAAC-3', (SEQ ID 3), 5'-CUACUUU-CUUAAUGGCUUA), (SEQ ID 4) polo-like kinase 1 (PLK1), 5'-CAACCAAAGUCG AAUAUUGAUU-3 (SEQ ID 5), 5'-CAAGAAGAAUGAAUACAGUUU-3'(SEQ ID 6), 5'-GAAGAUGUCCAUGGAAAUAUU-3', (SEQ ID 7), 5'-CAACACGCCUCAUCCUCUAUU-3', (SEQ ID 8), Kinesin superfamily protein (Kif11), 5'-CGUCUUUAGAUUC-CUAUAU-3'(SEQ ID 9), 5'-GUUGUUCCUACUUCA-GAUA-3'(SEQ ID 10), 5'-GUCGUCUUUAGAUUCCU AU-3'(SEQ ID 11), 5'-GAUCUACCGAAAGAGUCAU-3' (SEQ ID 12)], non-targeting siRNA 5'-UAGCGACAUUU-GUGUAGUU-3'(SEQ ID 13) (siTox), purchased from Dharmacon Inc, IL. This mixture was sonicated (Sonics, Vibracell) at 25° C. using two 15 second pulses at settings of 130 W, 20 k Hz, and 40% amplitude. The sonicated sample was centrifuged at 15,000×g for 5 minutes. The pellet comprising bundled SWCNT was discarded and the supernatant was transferred into a clean tube and centrifuged an additional 1 minute at the same settings. The resulting supernatant contained SWCNT non-covalently suspended by coatings of adsorbed siRNA. Near infrared (NIR) fluorescence spectroscopy indicated that the sample contained predominantly individually suspended SWCNT rather than nanotube aggregates.

The near infrared (NIR) emission spectrum of the siRNA-suspended SWCNT was measured using 658 nm excitation in a model NS1 NanoSpectralyzer (Applied NanoFluorescence, Houston, Tex.). NIR fluorescence microscopy was performed using a custom-built apparatus containing diode laser excitation sources emitting at 658 and 785 nm. Individual SWCNT internalized into cells were imaged with a custom-built NIR fluorescence microscope using 785 nm excitation, a 60× oil-immersion objective, and a 946 nm long-pass filter in the collection path. Bright field images were taken using the 60× objective.

The unagglomerated, SWCNT are made water-compatible by coating with siRNA. As shown in FIG. 1A, sonication of SWCNT in aqueous buffer in the absence of siRNA failed to produce a stable suspension. However, as shown in FIG. 1B, equivalent processing in the presence of siRNA provided stable, homogeneous suspensions. These suspensions displayed strong NIR fluorescence between approximately 900 and 1600 nm, as depicted in FIG. 1C, which is characteristic of dispersed or unagglomerated SWCNT.

The SWCNT/siRNA complexes were stable and retained their biological activity following 30 days of storage at 4° C. It is predicted that the SWCNT/siRNA complexes could retain biological activity following longer periods of storage at 4° C.

Example 2

Cell Culture and Cellular Incubation with SWCNT/siRNA Complexes

MiaPaCa2-HRE (a pancreatic cell line with a HIF-1α/luciferase reporter) cells were incubated in growth media consisting of high glucose DMEM supplemented with 10% fetal calf serum (FCS) (all reagents from HyCone). To determine the internalization rate of non-targeting siRNA-solubilized SWCNT, 50 µL of the complex (final SWCNT concentration approximately 1.25 mg/L) was added to cells (approximately $2 \times 10^5$ cells/well) that had been incubated for 18 hours in 1 mL of media in a 6-well plate. Incubation with the SWCNT/siRNA complex continued for 1, 3 and 6 hours. After incubation, media was removed from the wells, the cells were washed once in phosphate buffered saline (PBS) and then were detached from the surface by adding 0.25% trypsin (Invitrogen). The detached cells were washed with growth media to inactivate the trypsin and then washed again with PBS. The cells were resuspended in 1 mL of growth media, transferred onto a circular glass cover slip in a well of a new 6-well plate and incubated at 37° C. in a humid environment for approximately 20 hours. NIR fluorescence microscopy was utilized to identify internalized SWCNT.

The MiaPaCa2-HRE cell line was generated to stably express the promoter sequence of a target gene of HIF-1α comprising the HIF-1α binding hypoxia response element (HRE) fused to the luciferase gene. At the end of the experiment, 100 µL of media was removed from each well of the 96-well plate. The removed media was replaced with 50 µL of the luciferase reagent (25 mM tricine, 0.5 mM EDTA-$Na_2$, 0.54 mM sodium triphosphate, 16.3 mM $MgSO_4.7H_2O$, 0.3% Triton X-100, 0.1% w/v dithiothreitol, 1.2 mM ATP, 50 mM luciferin, and 270 mM coenzyme A). The plates were incubated at room temperature for 5 minutes. Sample luminescence was measured relative to a background control using a microplate reader (Polar Star Optima; BMG Labtech).

Cell proliferation reagent (WST-1, Roche, Mannheim Germany) was added to cells in media to a final concentration of 10% and the cells were incubated for 30 minutes at 37° C. in a humidified incubator. The absorbance of the sample was then measured relative to a background control using a microplate reader (Polar Star Optima; BMG Labtech) at 420-480 nm.

Statistical analyses were performed with commercially available software. Single regression analysis was used to assess the ratio of HIF-1 activity after treatment with 100 µL sample volume, SWCNT concentration approximately 4 mg/L, siRNA concentration approximately 2 µM, with the percentage luciferase expression after SWCNT/siRNA treatment as the dependent variable. Student's t-tests were used to compare the ratio of luciferase intensity within the tumor between mice treated with SWCNT/siRNA. Comparisons of mice treated with siRNA targeting HIF-1 (siHIF), SWCNT/non-targeting siRNA (SWCNT/SC), or SWCNT/siRNA targeting HIF-1α were computed by two-way analysis of variance (ANOVA). Statistical significance was defined as a P value of <0.05.

SWCNT were complexed with 20 µM of siRNA targeting polo-like kinase 1 (PLK1) in a 0.9% NaCl solution using the procedure described above. A 20 µL portion of each sample was added to cells (approximately $2 \times 10^5$ cells/well) in 100 µL of media containing 10% FCS in 96-well plates. The treated cells were incubated at 37° C. in a humid chamber for 72 hours and their viability was determined by the WST-1 assay.

To investigate the biological activities of SWCNT/siRNA complexes, 20 μL of each sample was added to cells (approximately 2×10⁵ cells/well) in 100 μL of media containing 10% FCS in 96-well plates. The plates were incubated at 37° C. in a humidified chamber for approximately 18 hours prior to and for 72 hours following addition of the complexes. To determine the ability of the complexes to suppress HIF-1α activity or silence the HIF-1α protein, treated cells incubated under normoxia for 72 hours were incubated for a further 18 hours under hypoxic conditions (1% oxygen).

Figure 2:
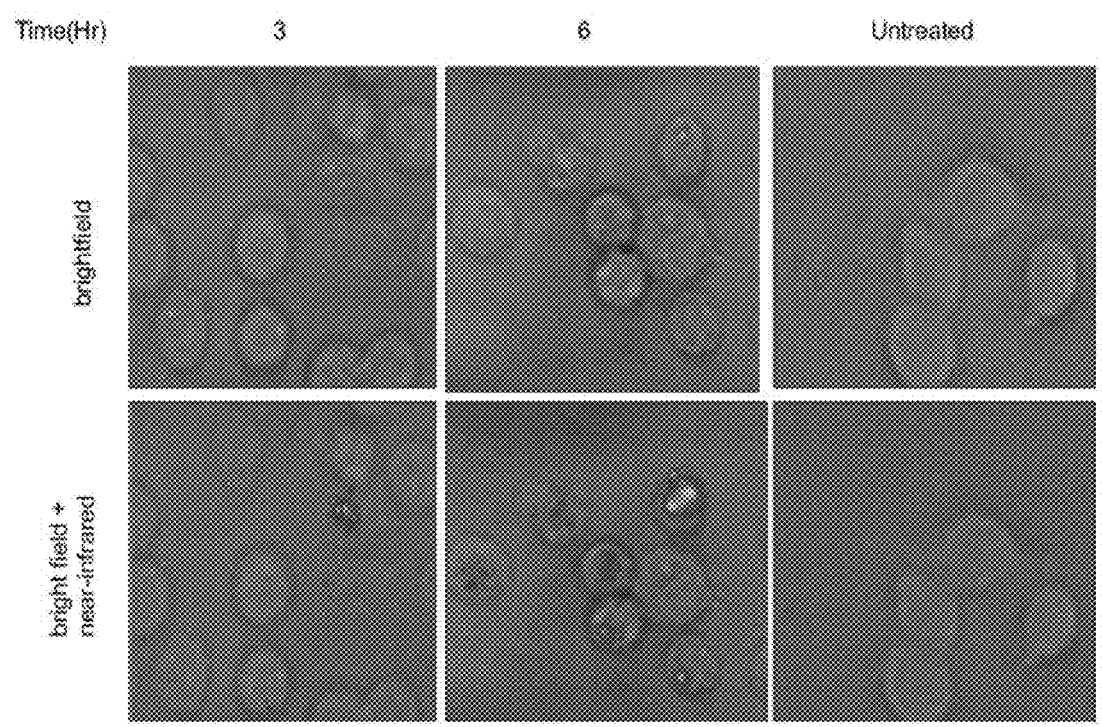
FIG. 2 includes bright field and near-infrared (NIR) images of incubated cells with internalized SWCNT.

MiaPaCa2-HRE cultures were exposed to SWCNT/siRNA complexes for 1, 3, and 6 hours to monitor internalization of the complex into tissue cells. As shown in FIG. 2, NIR fluorescence microscopy of the treated cells revealed internalized SWCNT. The cells having internalized SWCNT were characterized by their emission wavelengths and their strong dependence of emission intensity on excitation beam polarization. In addition, NIR fluorescent particles were found only in cells incubated with suspended SWCNT and not in SWCNT-free control samples. As the sample area irradiated by the laser beam was smaller than the image field, some cells in each image did not show NIR emission even though they contain internalized SWCNT. Incubation with the SWCNT/siRNA complexes for 1 hour resulted in SWCNT uptake by approximately 40% of cells. Incubation for 3 hours or 6 hours resulted in nanotube uptake by larger fractions of cells, and average SWCNT content per cell also increased with incubation time. Although the concentration of internalized nanotubes varied substantially from cell to cell, after 6 hours of incubation, more than 90% of the cells showed detectable SWCNT.

Figure 3:
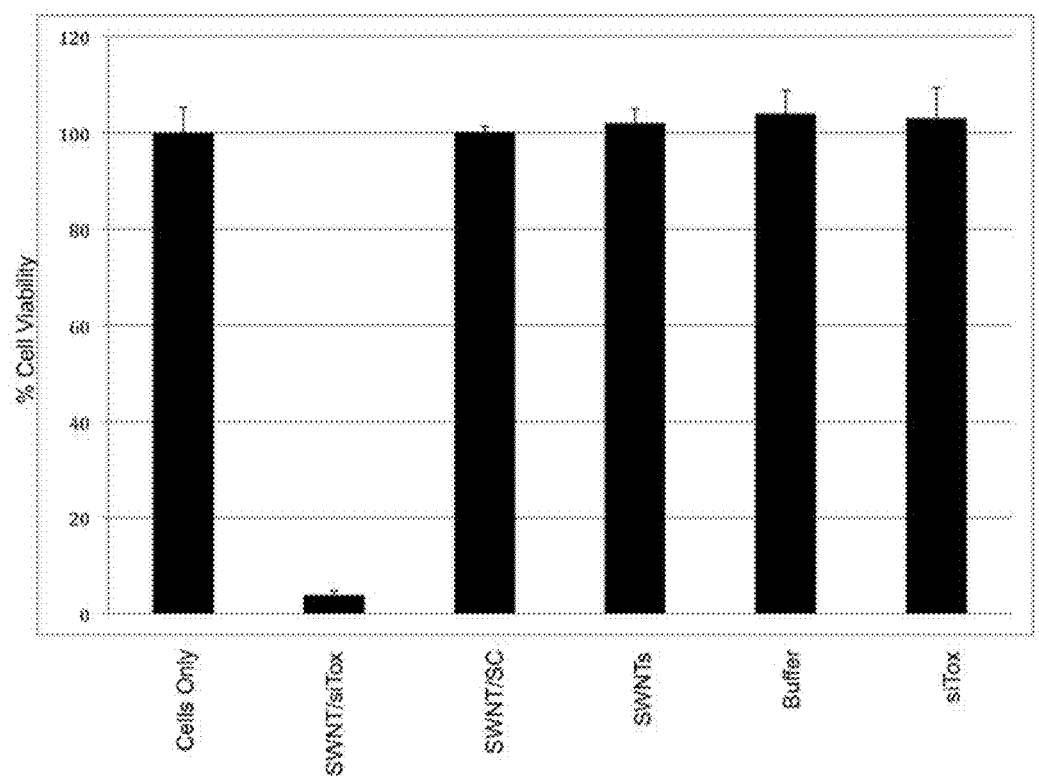
FIG. 3 graphically depicts the cell viability of MiaPaCa-HRE pancreatic cancer cells after delivery of biologically active siRNA via SWCNT.

A mixture of pristine SWCNT and siTox was sonicated and 20 μL of the complex (containing 5 mg/L SWCNT and 5 μM siTox) was added to MiaPaCa-HRE (human pancreatic cancer) cells growing in a 96-well plate. Each well contained 100 μL of medium with 10% FCS. Controls included untreated cells and cells treated with 20 mL of a complex of SWCNT and non-targeting siRNA (SWCNT/SC) (containing 5 mg/L SWCNT and 5 μM siSC), 20 μL of SWCNT solubilized by 10% FCS, buffer alone and free uncomplexed siTox (final concentration 5 μM). At 72 hours after treatment, a decrease of approximately 90% was observed in viability of cells treated with the SWCNT/siTox complex, as shown in FIG. 3. This effect was specific to the SWCNT/siTox complex, as none of the controls exhibited decreased cell viability. The preparative sonication did not damage the siRNA and siRNA was delivered into cells in a biologically active form. Further, the presence of serum did not inhibit the transfection process.

Figure 4:
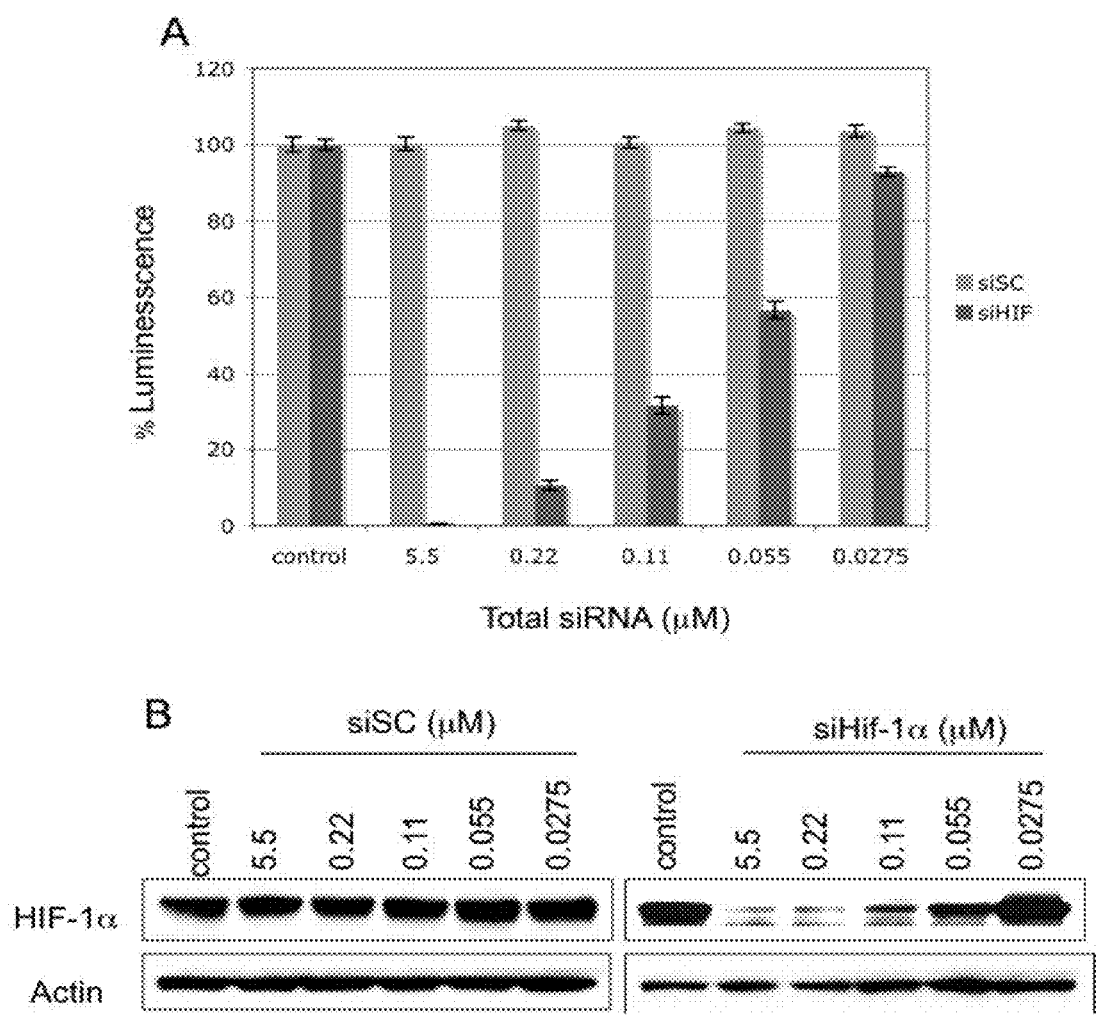
FIG. 4 graphically depicts inducement of RNAi response after delivery of siRNA into cells by SWCNT.

The ability of SWCNT/siRNA complexes to activate a specific RNAi response was tested in MiaPaCa-HRE pancreatic cancer cell line. Changes in HIF-1α activity were monitored in these cells by measuring the levels of luciferase expression. MiaPaCa-HRE cells were treated with SWCNT complexed with either an siRNA specifically targeting HIF-1α (siHIF), or a non-targeting siRNA (siSC), at final concentrations of 3 mg/L SWCNT and 5 μM siRNA. The final siRNA concentration was based on the initial siRNA concentration suspended in the siRNA buffer and, as such, the final siRNA concentration likely exceeded the actual concentration of siRNA complexed to SWCNT and the actual concentration taken into cells by SWCNT. Treated cells were incubated under normoxic conditions at 37° C. for 72 hours and then were transferred into a hypoxic chamber (1% oxygen) for an additional 18 hours. HIF-1 activity was found to be significantly inhibited in cells treated with the SWCNT-siHIF-1α complex, but unchanged in cells treated with the SWCNT/siSC complex, as shown in FIG. 4A. Western blotting, as shown in FIG. 4B, confirmed that the inhibition of HIF-1 activity was the result of knockdown of the protein. The loss of HIF-1 activity and protein knockdown correlated well in a concentration-dependent manner. Because knockdown of the HIF-1α protein was observed only in cells treated with SWCNT/siHIF-1α complexes, it is likely that siRNAs retain their ability to induce a specific RNAi response after delivery into cells by complexation with SWCNT.

Transfecting cells for periods longer than 6 hours with SWCNT/siRNA results in both a significant uptake of the complexes into the cells, as shown in FIG. 2, and silencing of HIf-1α expression, as shown in FIG. 4B. As such, the initial growth inhibition observed in our ex-vivo study was most probably due to the complete inhibition of HIF-1α.

Figure 5:
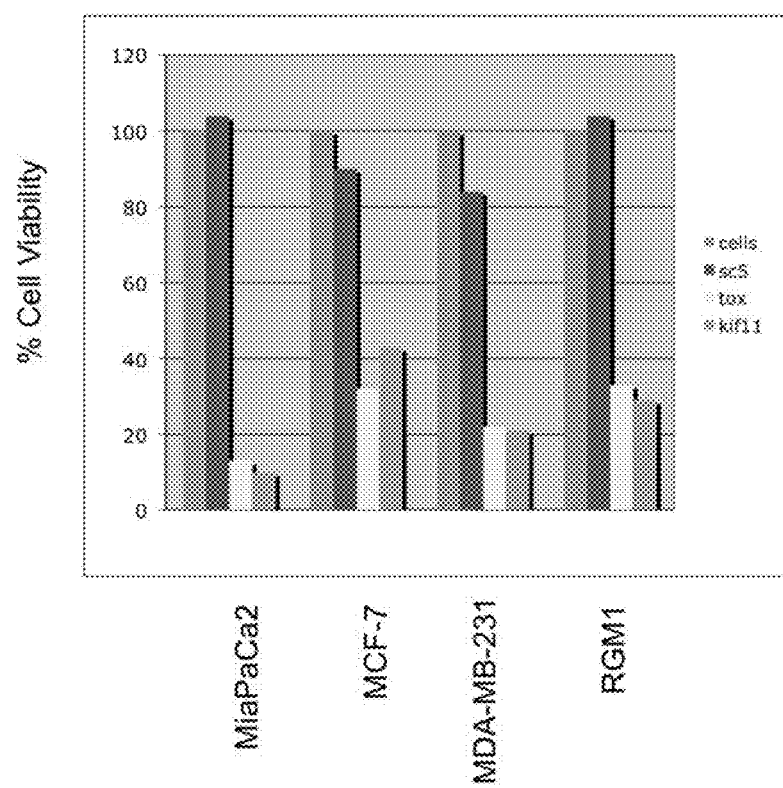
FIG. 5 graphically illustrates siRNA activity delivered into a variety of cancer cells by SWCNT induces RNAi response with similar efficiency.

Complexes of either SWCNT/non-targeting siRNA (siSC), SWCNT/siRNA targeting Kif11 (siKif11) or SWCNT/siRNA Tox (siTox) at a final concentration of 5 mM were added to cells growing in normal media containing 10% FCS. SWCNT/siRNA complexes were added to cultures of pancreatic cancer cells (MiaPaCa2), breast cancer cells (MCF-7, MDA-MB-231), and ovarian cancer cell line (RGM1) to determine if SWCNT could deliver siRNA into a wide range of cell types to induce the RNAi response. Cells were incubated at 37° C. for 72 h. Cell viability was determined by the WST-1 Assay. As shown in FIG. 5, non-targeting siRNA (siSC) demonstrated negligible toxicity to the cancer cells tested while siTox and siKif11 both induced cell death in transfected cells. These results suggest that SWCNT have the potential to function as a serum-insensitive, wide range transfection agent to deliver siRNA into cancer cells to induce the RNAi response.

Example 3

Injection of Mice with MiaPaCa-2/HRE Pancreatic Cancer Cells

The cells were grown in humidified 95% air, 5% $CO_2$ at 37° C. in DMEM supplemented with 10% FCS. Cells ($10^7$) in log cell growth were suspended in 0.1 mL Matrigel (Becton Dickinson Biosciences, Pal Alto, Calif.) and subcutaneously injected into the flanks of female Swiss nu/nu mice (Charles River laboratories, Wilmington, Mass.). Tumor diameters at right angles ($d_{short}$ and $d_{long}$) were measured twice weekly with electronic calipers and converted to volume by the formula: volume=$d_{short}^2 \times d_{long}/2$. When the tumors reached 150 mm³, the mice were stratified into groups of 8 animals having approximately equal mean tumor volumes. Intra-tumoral administration of the siRNA/SWCNT complexes was then performed twice per week for 3 weeks (100 μL sample volume, SWCNT concentration approximately 4 mg/L, siRNA concentration approximately 2 μM). The intra-tumoral injections were administered with the mice positioned dorsally and their tumors divided into four quadrants. Each injection was administered in a new quadrant using a clockwise rotation. Tumor volume was measured twice weekly until the tumor reached 1500 mm³ or more or became necrotic, at which time the mice were euthanized.

After 20 days of tumor development, mice were imaged twice weekly using the IVIS Lumina (Caliper Life Sciences). Mice were pair-matched into groups according to their tumor volumes. Before imaging, D-Luciferin (Caliper Life Sciences) was given to each mouse via intraperitoneal injection at a dose of 150 mg/kg and allowed to distribute for 5 minutes. The mice were anesthetized in the chamber with 3% isoflurane and then imaged using a 12.5 cm field of view and a 15 second exposure time. Their respective bioluminescence intensities were determined by calculating the photon flux using Living Image software (version 3.0). Photon flux was represented as photons/s/cm$^2$/sr in the region of interest (ROI) and surrounding bioluminescence signal provided by the tumor. The ROIs were then used to determine the photon flux, expressed as percent photon flux of vehicle control values.

Cell pellets were resuspended in modified RIPA lysis buffer (10 mM NaCl, 1% NP-40, 0.5% sodium deoxycholate, 0.1% SDS, 50 mM tris-hydrochloric acid [pH 7.5]) with inhibitors (20 μg/mL aprotinin, 1 mM sodium fluoride, 2 mM sodium orthovanadate, 0.5 mM phenylmethanesulfonyl fluoride, and 250 mg/mL benzamidine) in ice for 30 minutes and centrifuged at 15 000×g for 30 minutes to collect whole cell lysates. The lysates (50-60 μg) were run on 10% SDS-polyacrylamide electrophoresis (PAGE) gels and transferred to a polyvinylidene difluoride membrane. Western blotting was performed with specific primary antibodies and peroxidase-conjugated affiniPure anti-Mouse and anti-Rabbit secondary antibodies (Jackson ImmunoResearch Laboratories). Proteins were visualized with ECL Plus enhanced chemiluminescence reagents (Amersham Biosciences, Piscataway, N.J.).

Figure 6:
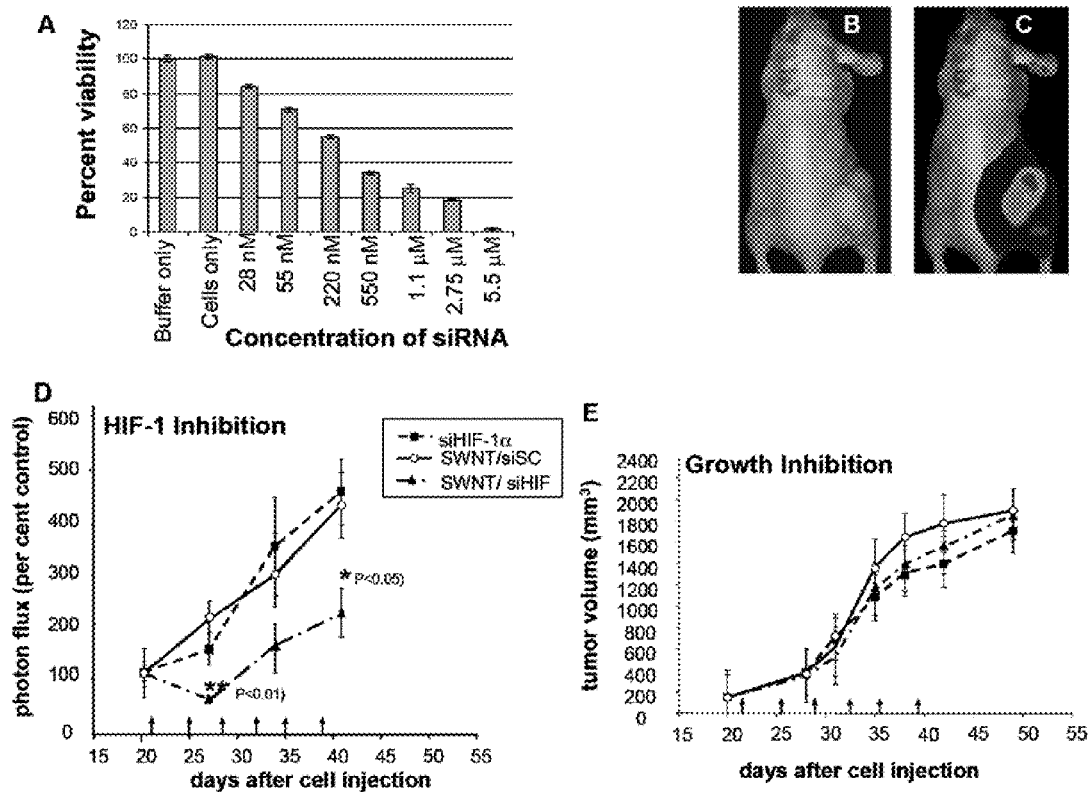
FIG. 6 shows the inhibition of HIF-1α activity in a xenograft mouse tumor after administration of SWCNT/siRNA complexes.

FIGS. 6A-6E illustrate the inhibition of HIF-1α activity in a xenograft mouse tumor after administration of SWCNT/siRNA complexes. In particular, the xenograft mouse tumor model was utilized to investigate the ability of SWCNT/siHIF complexes to inhibit HIF-1α activity in vivo. An 0.9% saline solution was utilized as an alternative to the siRNA buffer. In order to demonstrate that a similar biological outcome using siRNA/SWCNT complexes in 0.9% saline can be achieved, complexes in saline were prepared at several concentrations, as described for the siRNA buffer and added to MiaPaCa-HRE pancreatic cancer cells growing in normal media containing 10% FCS. siRNA targeting Polo-like Kinase 1 (PLK1), a protein that plays an important role in the G2-M transition and whose silencing results in cell death, was utilized. As shown in FIG. 6A, the saline environment provided no significant change in biological activity of the SWCNT/siRNA complexes at concentrations used for the animal study.

To study the effectiveness of targeting MiaPaCa-HRE cells in vivo, cell suspensions were subcutaneously injected into the right flanks of 6 to 8-week-old female athymic nude mice (nu/nu). Activation of HIF-1α in the hypoxic environment of the growing tumor was confirmed by imaging the bioluminescence of luciferin. Because MiaPaCa cell lines do not express HIF-2a, the images allowed HIF-1α activity to be monitored in vivo in the xenograft mouse model, as depicted in FIGS. 6B and 6C. Red indicates the highest luciferase concentration, followed by yellow and green, while blue represents bleed-through. Significantly decreased tumor HIF-1α activity was observed in mice treated with SWCNT/HIF complexes compared to those treated with complexes comprising either the control SWCNT/siRNA (p<0.01 to p<0.05) or HIF-1α siRNA alone (FIG. 6D). However, no suppression of tumor volume was observed (FIG. 6E), a result possibly attributable to incomplete inhibition of HIF-1α. To test this possibility, an ex-vivo experiment was conducted in which MiaPaCa-HRE parental cells, cells transfected with a control siRNA/SWCNT complex, and siHIF/SWCNT complex were grown in tissue culture for 24 hours prior to being injected subcutaneously into mice. Tumor growth was monitored over a period of 33 days. It was observed that tumors generated by the parental cells and those transfected with the control siRNA grew similarly and at a faster rate compared to tumors transfected with the siRNA targeting HIF-1α. An initial period of growth inhibition of the tumors transfected with the siRNA targeting HIF-1α accounted for the slow rate of growth compared to the other two groups. No significant difference in the levels of HIF-1α was observed between the three groups. This may be due at least in part because protein silencing by siRNA is a transient effect, usually lasting up to about one week.

Even at high concentrations, toxicity was not observed following intravenous administration of either SWCNT or coated SWCNT of the present invention. No mortality or loss of weight of mice as well as no evidence of toxicity in tissues and organs were observed in these studies that ranged in time from 24 hours to 6 months after treatment.

The results demonstrate that siRNA can be used to solubilize SWCNT and that noncovalent SWCNT/siRNA complexes can transfect cancer cells and effectively silence a targeted gene in cell culture and also in tumors in vivo. In addition, siRNA can be used to silence target genes with a high degree of specificity. The results further demonstrate that numerous siRNA sequences can be utilized to complex the SWCNT and that irrespective of their nucleotide sequences, the siRNA solubilized the SWCNT equally effectively. This observation differs from observations that the ability of single stranded DNA to solubilize SWCNT is dependent on the guanine-cytosine (GC) content of the nucleotide sequence.

Efficient intracellular transport and delivery of siRNA is critical to the potency and in vivo therapeutic activity of RNAi. Internalization of the SWCNT/siRNA complex was observed in about 30% of the treated cells 1 hour after addition of the complex to cells growing in media containing 10% serum. By 3 hours post treatment, internalized SWCNT were observed in more than 90% of cells and the number of internalized SWCNT per cell increased further by 6 hours. These findings may suggest the capability of introducing siRNA into nearly all of the cells in culture.

There are significant differences between SWCNT and lipid reagents as delivery agents of siRNA. Commercial lipid reagents are cell line specific and to obtain optimum transfection conditions with minimum toxicity requires selecting the best reagent from a panel of lipid reagents. The SWCNT are much less cell line dependent and have negligible toxic effects on most cell lines. In addition, lipid reagent transfections generally have to be carried out in the absence of serum, which is toxic to cells. Conversely, SWCNT transfections of the present invention can be carried out in the presence of serum.

The sonication protocol for forming SWCNT/siRNA complexes does not functionally damage the siRNA, as cells exposed to the complexes display a clear RNAi response. Both HIF-1α activity and protein levels were lowered by approximately 70% to 80% when the SWCNT delivered siRNA targeting HIF-1α mRNA into the host cancer cells. One possibility is that siRNA dissociates from the SWCNT inside the cell; another is that siRNA molecules retain their RNAi activity while complexed with the SWCNT.

Example 4

Characterization of SWCNT/siRNA Complexes

Figure 7:
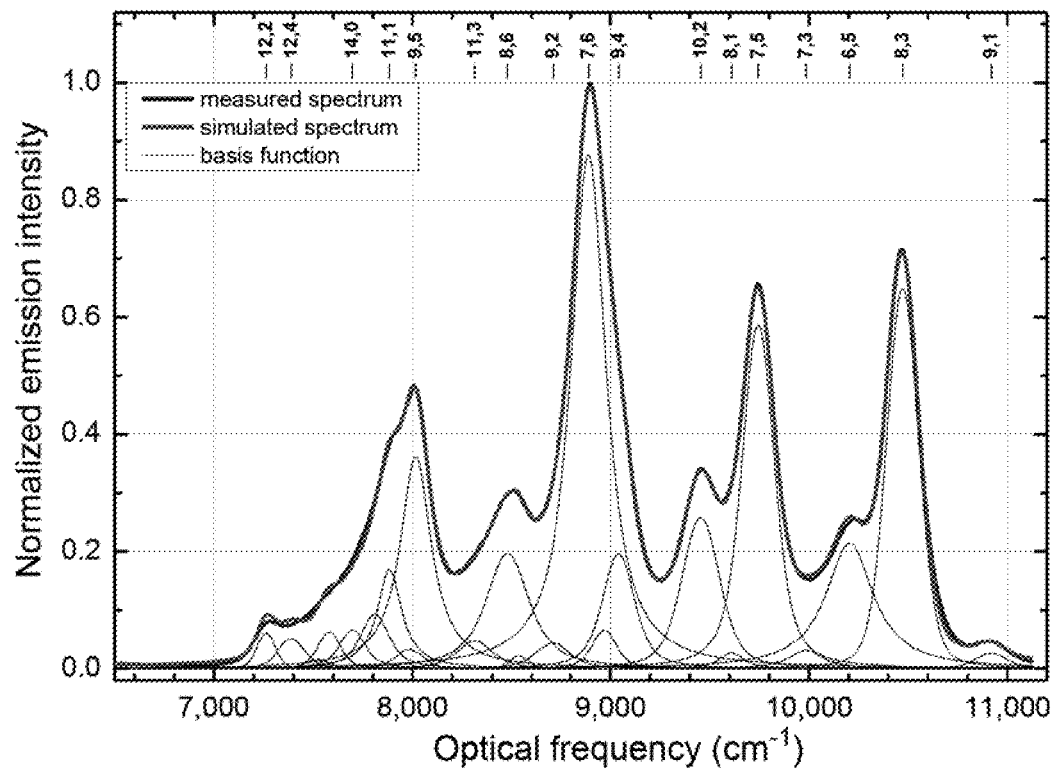
FIG. 7 shows mixed SWCNT samples near-IR fluorescence that is a superimposition of peaks from the various structural forms that are present.
Figure 8:
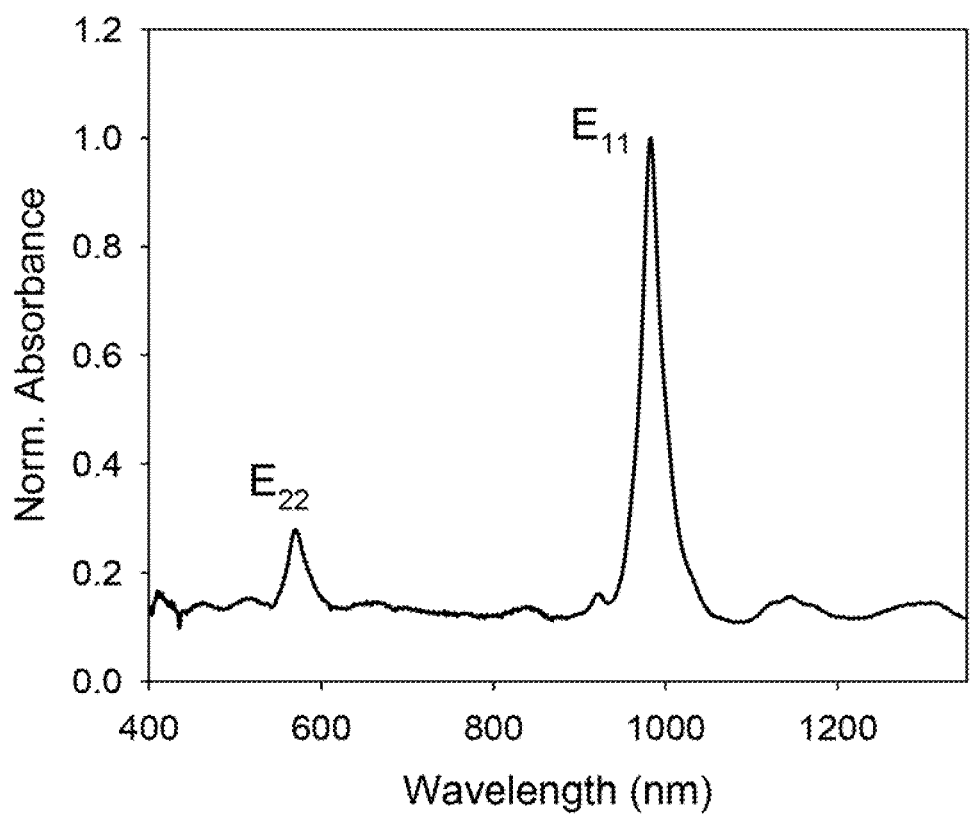
FIG. 8 shows a sorted SWCNT sample with a greatly simplified absorption spectrum because only one structural form is present.
Figure 9:
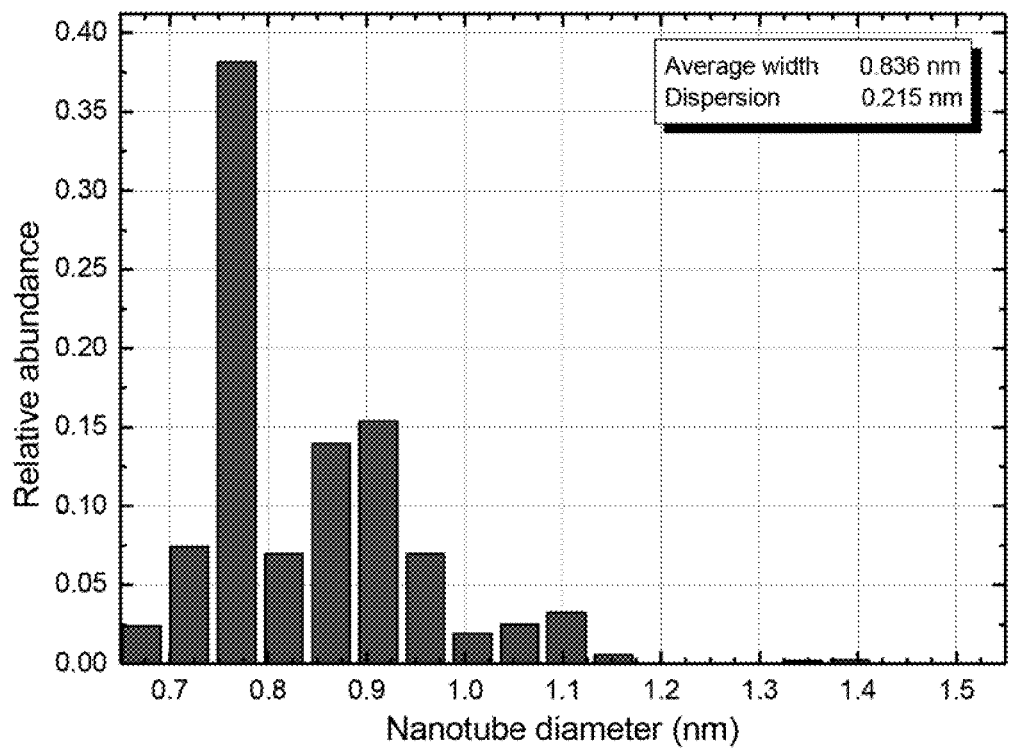
FIG. 9 is a bar graph showing SWCNT diameter distribution deduced from fluorometric analysis.

Single walled carbon nanotubes (SWCNT) were produced using HiPco, in which high pressure CO is disproportionated on Fe nanoparticles formed in the gas phase from $Fe(CO)_5$ decomposition. This method generates the cleanest product of single versus multi-walled nanotubes with relatively small diameter nanotubes that have strong near-IR spectral transitions within the 850 to 1600 nm. Samples used for biological work are composed of SWCNT with a diameter of approximately 1 nm and lengths from 100-400 nm. Near-Infrared spectral analyses allows the determination of the composition of the sample with respect to nanotube size distribution, purity, concentration in solution and individualization. FIG. 7 shows mixed SWCNT samples having near-IR fluorescence that is a superposition of peaks from the various structural forms that are present, and as shown in FIG. 8, a sorted SWCNT sample shows a greatly simplified absorption spectrum because only one structural form is present. Arrows indicate areas of tube diameters. Diameter<1 nm: area of bare SWCNT; >1 nm: area of SWCNT with complexed siRNA. FIG. 9 shows the diameter distribution of mixed SWCNT determined using fluorometric analysis.

Figure 10:
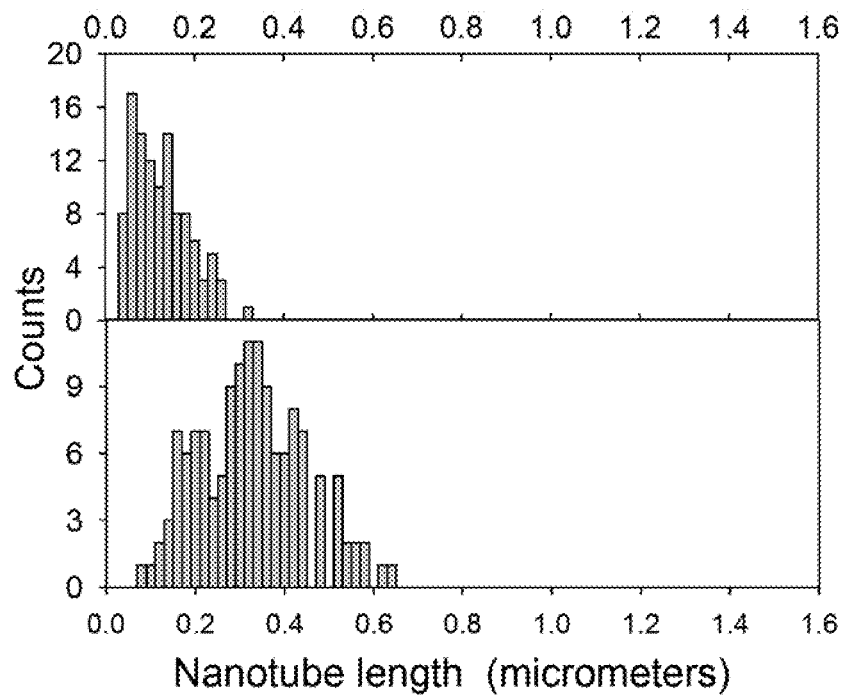
FIG. 10 is a bar graph showing SWCNT length distributions as measured by atomic force microscopy for two difference fractions obtained in an electrophoretic length sorting process.

Raw SWCNT samples (lengths of 50 nm to 1200 nm) were solubilized by sonication for 10 min using horn sonicator 80 W with a 50% duty cycle in sodium dodecyl sulfate 0.5% solution (NaDOC) and subjected to electrophoretic current +15 kV applied current to provide samples with lengths distributions. The length distribution of each sample was determined using atomic force microscopy. FIG. 10 shows that each sample exhibited median lengths of 200 nm (25 to 250 nm) and 400 nm (100 to 600 nm). Similar length separation has been afforded through modification of sonication procedures to provide samples of different average length of SWCNT. Biological activity and toxicity of samples have been undertaken with these samples to determine the optimum sample characteristics.

SWCNT sample preparation is critical for both fluorimetric analysis and biological utility. Nanotubes have a strong tendency to aggregate into tight bundles bound by van der Waals forces, and the electronic interactions within SWCNT bundles cause fluorescence quenching, making accurate analytical analyses impossible. Additionally, SWCNT solutions must be well dispersed to achieve adequate biological activity. To disaggregate raw samples of SWCNT to obtain dispersions of individually suspended nanotubes, aqueous surfactant solutions are used with ultrasonic agitation. Physical properties of the surfactant solutions are also important for analytical purposes, because emission intensities and spectral peak positions can be affected by the immediate environment of the nanotube. Sample concentrations for current biological activity analyses are in the of order several mg of SWCNT per liter up to 1 mg/mL.

Raw HiPco SWCNT product was added to an aqueous buffer solution (100 mM KCl, 30 mM HEPES-KOH [pH 7.5], 1 mM $MgCl_2$) containing 20 μM solubilized pooled siRNA. This mixture was sonicated (Sonics, Vibra-cell) at 25° C. using two 15 second pulses at 130 W, 20 k Hz, and 40% amplitude with 45 second icing periods between sonication for a total of 2 minutes. The sonicated samples were centrifuged at 15,000×g for 5 min, and the pellet including bundled SWCNT was discarded. The supernatant containing dispersed soluble SWCNT noncovalently suspended by coatings of adsorbed siRNA was transferred into a clean tube and centrifuged an additional 1 min at the same settings. NIR fluorescence spectroscopy is used to ensure that these samples contained individually dispersed SWCNT rather than nanotube aggregates. The sonication used for the dispersion and complexation of the siRNA to SWCNT has been found not to reduce the biological activity of the siRNA. Complexation of SWCNT with siRNA produced an adequately dispersed, stabile solution that remained biologically active for 30 days or more when stored at 4° C.

The NIR emission spectrum of the siRNA-suspended SWCNT was measured using 658 nm excitation in a model NS1 NanoSpectralyzer (Applied NanoFluorescence, Houston, Tex.). NIR fluorescence microscopy was performed using a custom-built apparatus containing diode laser excitation sources emitting at 658 and 785 nm. Individual SWCNT internalized into cells were imaged with a custom-built NIR fluorescence microscope using 785 nm excitation, a 60× oil-immersion objective, and a 946 nm long-pass filter in the collection path. Bright field images were taken using the 60× objective.

Figure 11:
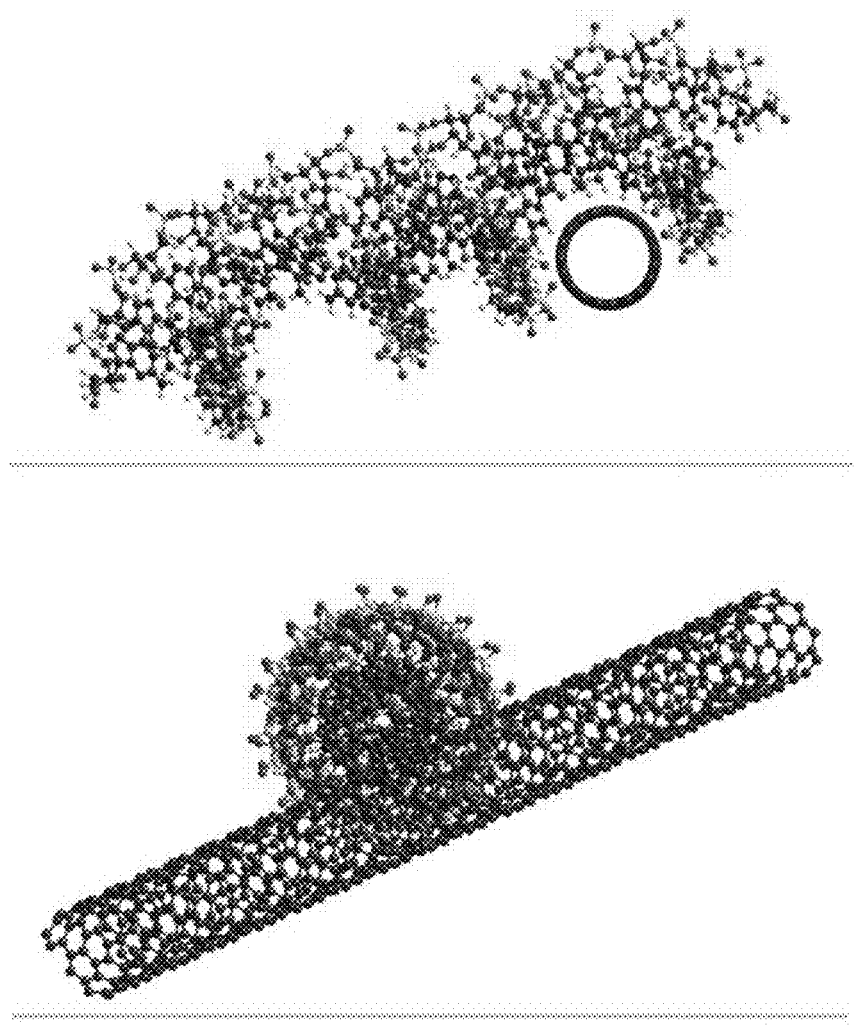
FIG. 11 shows a computer generated model of SWCNT/siRNA complexes.

A computer model of our siRNA complexed to the SWCNT was prepared as shown in FIG. 11. The models are displayed A: along SWCNT axis; B: along siRNA axis. The model suggests that the SWCNT fits into the major groove of the siRNA helix with the siRNA projecting out from to the axis of the tube. This model suggests that siRNA that is delivered into cells may be accessed and processed while it still is complexed to the SWCNT. It also is possible that the siRNA is released from the SWCNT when internalized, however our data suggests that the siRNA/SWCNT complex is stable even in the presence of high BSA concentration. Therefore, it may enters the cell and is either slowly released or remains associated with the nanotube while processed.

Figure 12:
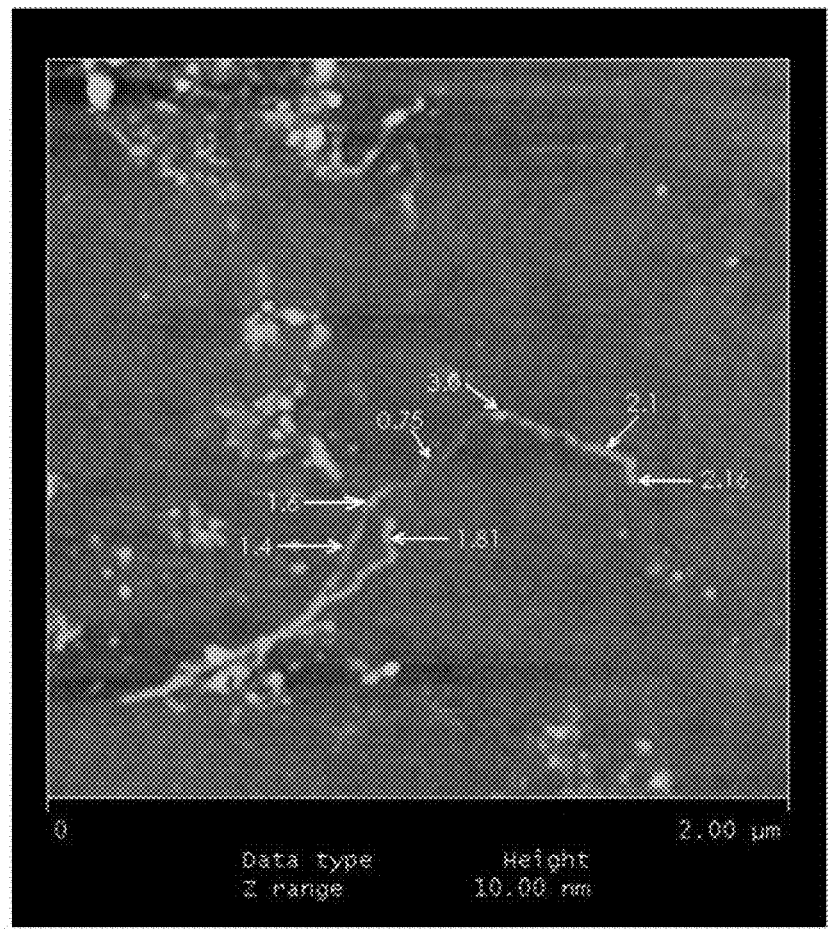
FIG. 12 shows Atomic Force microscopy illustrating SWCNT coated with siRNA. Arrows indicate areas of tube diameters. Diameter<1 nm: area of bare SWCNT; >1 nm: area of SWCNT with complexed siRNA.
Figure 13:
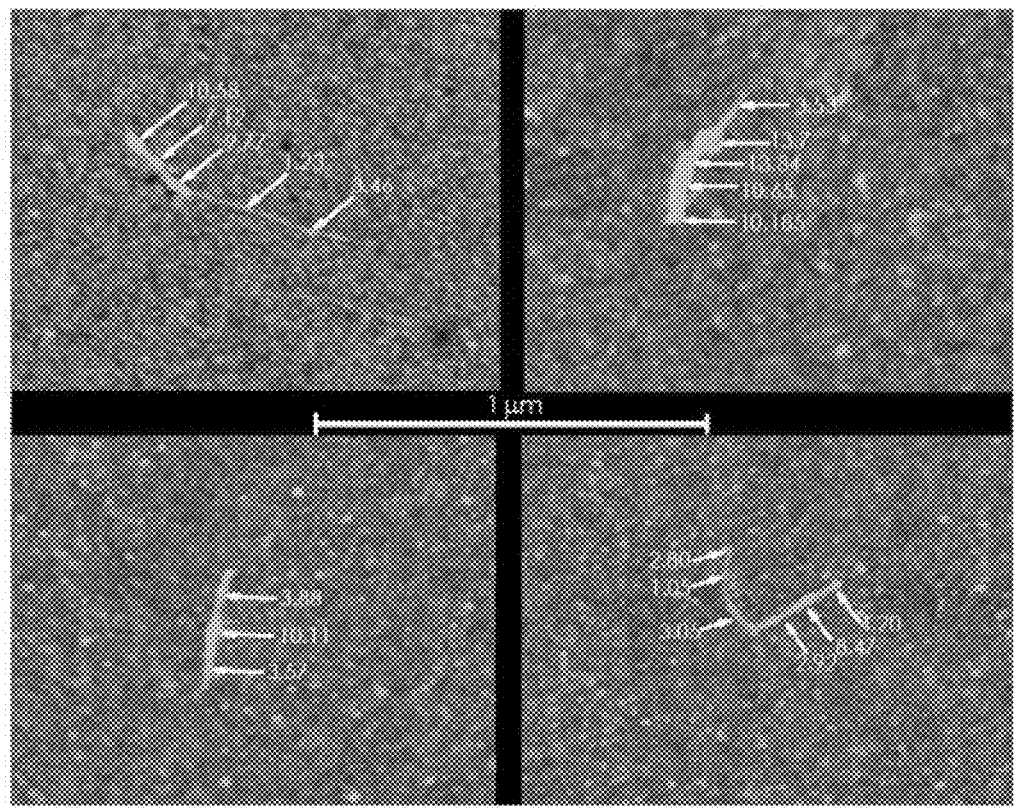
FIG. 13 shows Atomic Force microscopy (AFM) of SWCNT coated with siRNA that had been exposed to 1% BSA. Arrows indicate areas of tube diameters. Diameter<1 nm: area of bare SWCNT; >1 to 4 nm: area of SWCNT with complexed siRNA; >5 nm: area of SWCNT complexed to BSA.

FIGS. 12 and 13 are Atomic Force microscopy (AFM) images of SWCNT that were coated with siRNA (FIG. 12) before or after subsequent exposure to 1% BSA (FIG. 13). In FIG. 12, the arrows indicate areas of tube diameters, and show areas of bare SWCNT (<1 nm) and area of SWCNT with complexed siRNA (>1 nm). In FIG. 13, the arrows identify areas of bare SWCNT (<1 nm) areas or SWCNT covered with siRNA (>1 nm to 4 nm) and areas where BSA have associated with the SWCNT (>5 nm). This demonstrates that even in high concentrations of BSA the siRNA remains complexed to the SWCNT suggesting the siRNA/SWNCT complexes will have good stability when administered systemically.

Displacement data suggests that siRNA solubilized SWCNT slowly become further complexed with BSA with a saturation time of approximately 30 to 40 min. Taken together with the AFM data, the saturation point appears to be reached when BSA has fully complexed to portions of the SWCNT where no siRNA has complexed. To date, it appears that BSA does not easily displace the siRNA that is complexed to the nanotubes prior to BSA exposure.

Example 5

Reduction in Expression in Cell Culture

MiaPaCa wt cells ($1\times10^5$) were seeded into 6-well plate and allowed to attach for 24 hr in media containing 10% FCS 1000 μL. A solution of anti-thioredoxin siRNA ((Trx)siRNA, 23.5 ng/μL) was complexed with SWCNT as in Example 4 to provide a final SWCNT/(Trx)siRNA in 0.9% NaCl solution containing 2.4 ng/μL SWCNT and 4.7 ng/μL of siRNA. A time course for thioredoxin inhibition by the SWCNT/(Trx) siRNA was determined by providing 150 μL of this SWCNT/(Trx)siRNA solution to each well and incubating the treated cells for 1 hr, 3 hr, 6 hr or 24 hr. The media containing the SWCNT/(Trx)siRNA complexes was removed at the appropriate time and replaced with 2 mL of 10% FCS media. The cells were again incubated for 72 hr before evaluating for the cells for thioredoxin content by Western blotting (FIG. 14A). These data show that SWCNT can readily transfect siRNA into cells and uptake occurs within about 1 hr as a reduction in thioredoxin expression began within about 1 hr. This inhibition appears to increase over the 24 hr exposure to the SWCNT/(Trx)siRNA complex.

Figure 14:
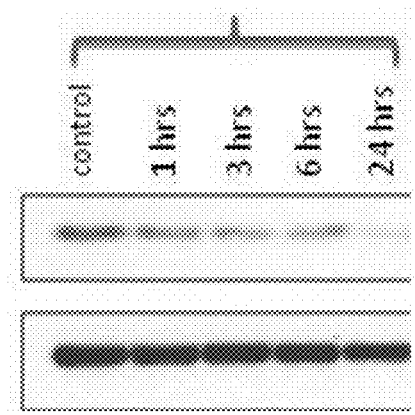
FIG. 14 shows Western blots obtained from cultured MiaPaCa cells that were exposed to SWCNT/(Trx)siRNA.
Figure 14:
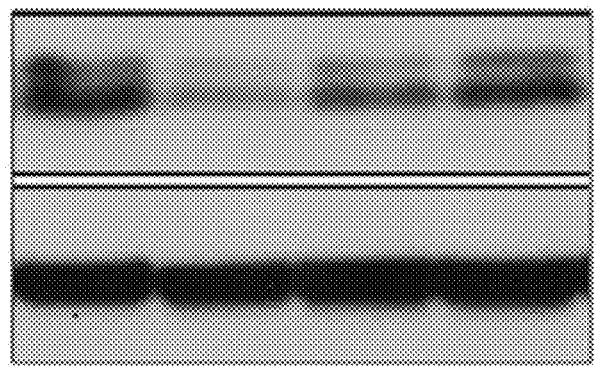

A dose dependent reduction in thioredoxin expression as a result of exposure to SWCNT/siRNA complex was shown by providing increasing concentrations of SWCNT/siRNA complex to MiaPaCa cells. In this example, 1 mL media containing increasing concentrations of SWCNT/(Trx)siRNA complex 1.76 to 4.83 ng/μL was added to each well of a plate, and the cells were incubated for 24 hr (FIG. 14B). The media was then removed and fresh media was added and the cells harvested for Western blotting 72 hr later. FIG. 14B shows reduction in thioredoxin expression in MiaPaCa cells exposed to SWCNT/(Trx)siRNA even when the SWCNT/(Trx)siRNA complex is provided at a low concentrations (50 μl). These data also show that higher concentrations of SWCNT/(Trx) siRNA may provide improved siRNA mediated inhibition of thioredoxin expression. Thus, these cell culture data of FIG. 14 shows both a dose dependent knockdown of thioredoxin protein (siRNA target) levels in as well as a time dependent knockdown.

Figure 15:
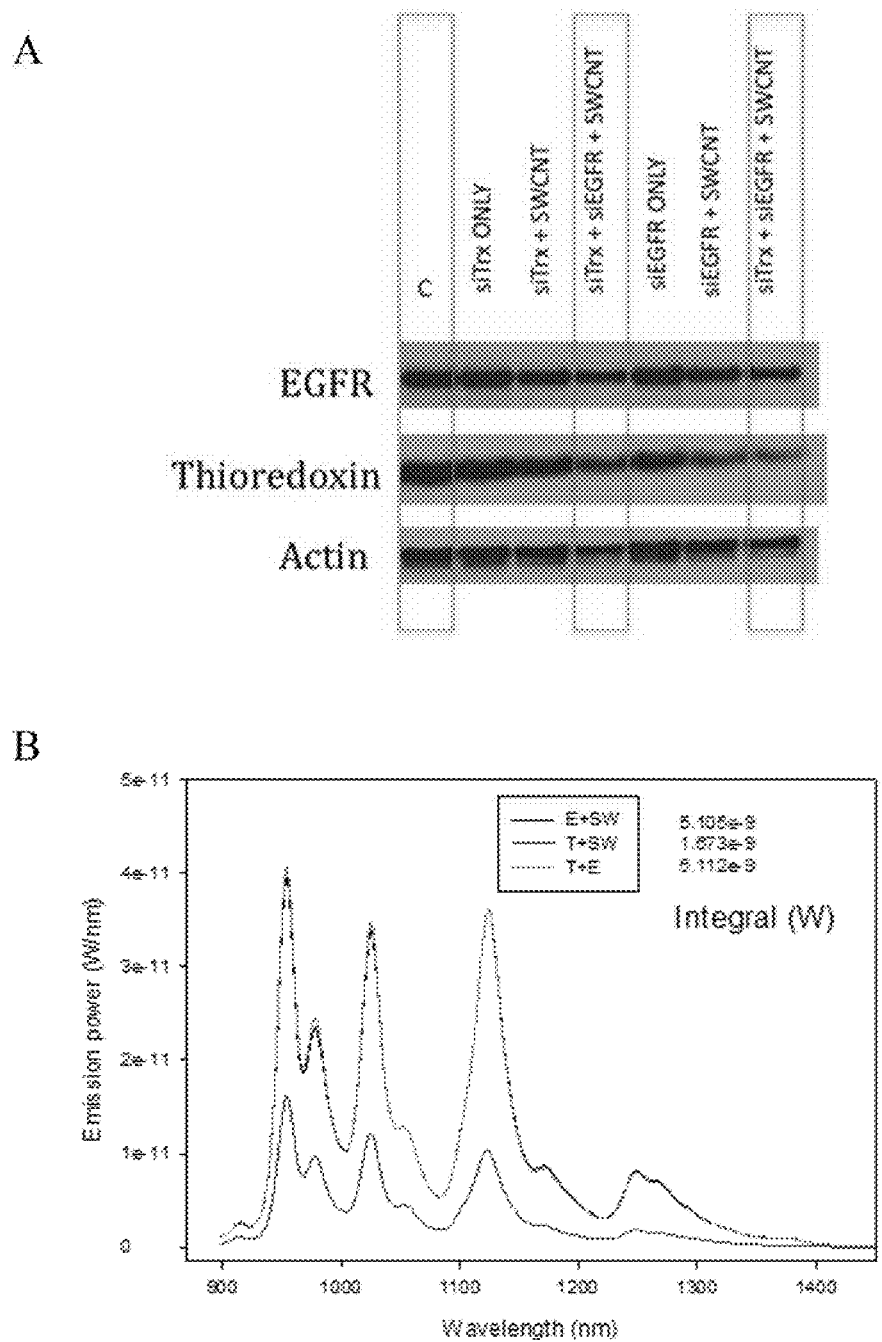
FIG. 15 shows a Western blot resulting from exposure of cultured MiaPaCa cells to SWCNT/(Trx)siRNA, SWCNT/(EGFR)siRNA, and SWCNT/(Trx)siRNA/(EGFR)siRNA dual payload SWCNT (FIG. 15A).

The effectiveness of SWCNT complexed with multiple siRNA was explored by complexing individual siRNAs directed toward Trx and EGFR with SWCNT either individually (single payload) or together (dual payload). MiaPaCa cells in culture were then exposed to the increasing concentrations 0.78 to 3.2 μg/mL of the complexes for 24 hr, the media changed, and then the cell were incubated for 72 hrs before being harvested, and Western blots performed on lysates. Each sample showed well dispersed SWCNT (FIG. 15B). Complexes including individual anti-Trx showed a concentration dependent reduction in Trx expression, and complexes including anti-EGFR siRNA showed a concentration dependent reduction in EGFR expression. Complexes including both anti-Trx and anti-EGFR siRNA showed a simultaneous concentration dependent reduction in both Trx and EGFR expression. Thus, single payload and dual payload SWCNT/siRNA complexes produced knockdown of Trx and/or EGFR (FIG. 15A showing cells treated with 0.78 μg/mL).

Example 6

Preparation of SWCNT for Systemic Delivery

Figure 16:
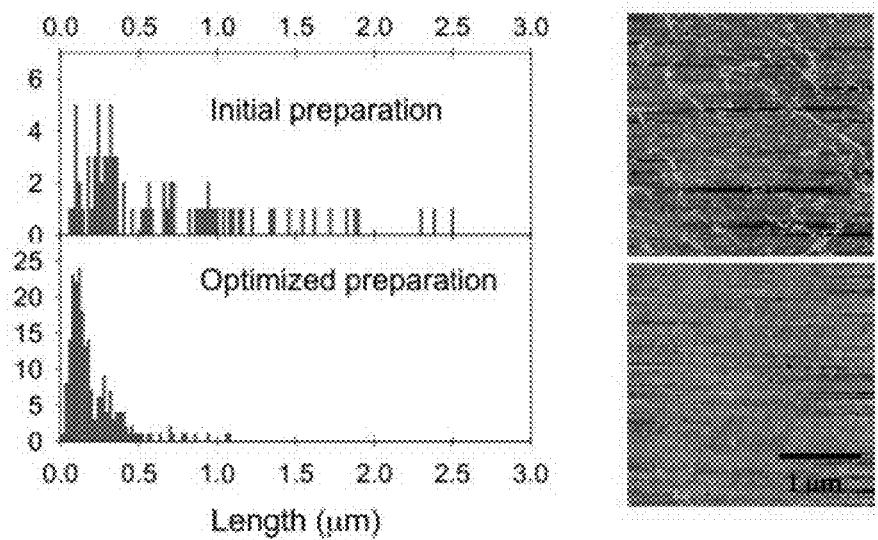
FIG. 16 shows a comparison of the size distribution of an initial preparation of SWCNT and a corresponding AFM (top), and the size distribution of an optimized preparation of SWCNT and corresponding AFM (bottom).

Raw HiPco SWCNT were dispersed in an aqueous solution using bio-compatible surfactant PLURONIC™ (F127). SWCNT (15.0 mg) in 15 mL of 1.0 mg/mL pluronic solution (3% w/v) in a 20 ml glass bottle was dispersed by 1.5 hr bath sonication (Sharpertek, Stamina XP) at 25° C. After bath sonication 15 mL sample was split into eight 2 mL eppendorf tubes and centrifuged at 13,000×g for 1 hr in a bench top centrifuge (Baxter Scientific, Biofuge-13) to remove impurities such as catalytic metal residue and other insoluble impurities and aggregated SWCNT bundles. The resulting dispersed solution of SWCNT was collected and the nanotube concentration was measured using a NanoSpectralyzer. A 20 μL aliquot of the SWCNT solution was diluted 20 times in water and utilized for optical measurements. FIG. 16 shows a sample optimization and size distribution of SWCNT in solution as prepared above. When initially dispersed, solution contains nanotubes in lengths up to 2500 nm. Optimized preparations have majority of SWCNT with lengths of 200 nm. An AFM for the initial preparation and the optimized preparation are provided to the right. The average SWCNT concentration for the optimized preparation was estimated to be about 500 mg/mL and used for the mice study.

Figure 17:
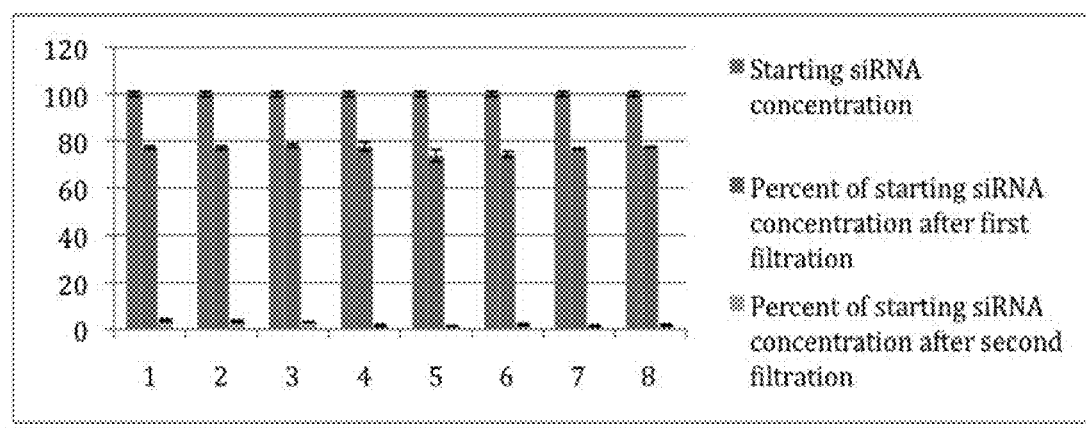
FIG. 17 shows the percent siRNA in stock solution before and after complexing with SWCNT and the amount of siRNA remaining in solution after complexing in eight identical preparations.

An siRNA stock solution was prepared in 0.9% NaCl at 100 μg/mL. The concentration of the solution was measured by nanodrop providing a 210/180 ratio. This solution (1 mL) was combined with eight samples of 100 μg SWCNT prepared as described above each in 2 mL eppendorf tubes and solubilization was undertaken using standard sonication procedure (Example 4). The solutions were centrifuged to remove any bundled or non-solubilized SWCNT. The resulting solution containing 38 μg/mL SWCNT was then filtered using Nanosep 100K cut off filter (Pall Life Sciences) to remove the complexed SWCNT from the remaining siRNA in solution. The siRNA concentration of the filtrate was again measured by nanodrop, and the percent of starting siRNA concentration was determined. The filter was washed with an additional 1 mL of 0.9% NaCl and a second reading was taken to determine whether residual siRNA remained trapped by the SWCNT versus complexed to SWCNT. The results are reported in FIG. 17. The SWCNT removed 20 to 25% of the siRNA from the solution equivalent to 20 to 25 μg. Hence, the resulting complex carried 0.53 to 0.66 μg siRNA per 1 μg SWCNT.

Example 7

Toxicology and Pharmacokinetics of SWCNT

To evaluate toxicity at 24 hr and 1 week following SWCNT administration, six (6) week old C57B16 mice were administered a single 200 μL i.v. dose of 50 and 100 μg SWCNT (7.5 mg/m$^2$ and 15 mg/m$^2$) in 3 w/v % pluronic. This dose is equivalent to 15 and 30 mg total dose in humans. The following groups were treated as follows:

Grp 1.—Untreated control 6 mice untreated

Grp 2.—Vehicle treated control 6 mice single IV dose vehicle (3% aqueous pluronic F127)

Grp 3.—SWCT treated 6 mice single IV dose of SWCNT solution: 50 mg in 100 mL.

Grp 4.—SWCT treated 6 mice single IV dose of SWCNT solution: 100 mg in 100 mL.

One set of 3 animals from each of the 4 groups of mice were sacrificed 24 hours after treatment, and a second set of 3 animals were sacrificed 1 week after the single treatment. Animals were euthanized in $CO_2$, and blood was drawn by cardiac puncture and placed into a tube for (i) hematology tests including complete CBC and white blood cell differential count and (ii) blood chemistry tests including tests for kidney function using creatinine and blood urea nitrogen (BUN) and liver function using aspartate aminotransferase (AST or SGOT) and alanine aminotransferase (ALT or SGPT).

Figure 18:
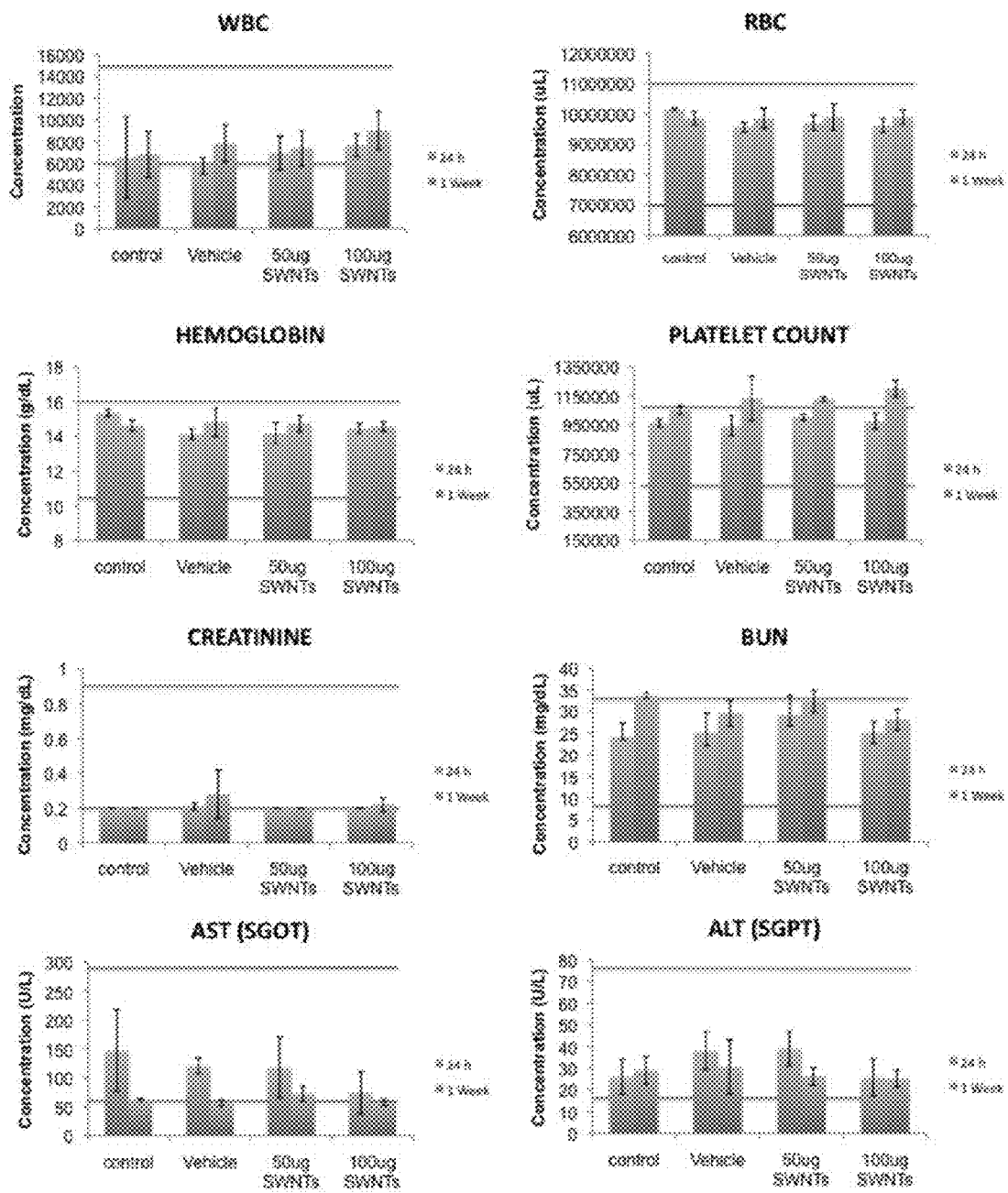
FIG. 18 shows the blood chemistry and hematology results 24 hours and 1 week after intravenous administration of 100 μg of optimized SWCNT.

There were no statistically significant changes in blood hematology or chemistry observed at either 24 hrs or 1 week following i.v. injection of either 50 μg of SWCNT or 100 μg of SWCNT. As indicated by FIG. 18 all measurements were found to have no difference from control values, and all samples were within the normal range for each parameter illustrated with the red lines. Accordingly, blood chemistry and hematology at both time points were in normal range.

Figure 19:
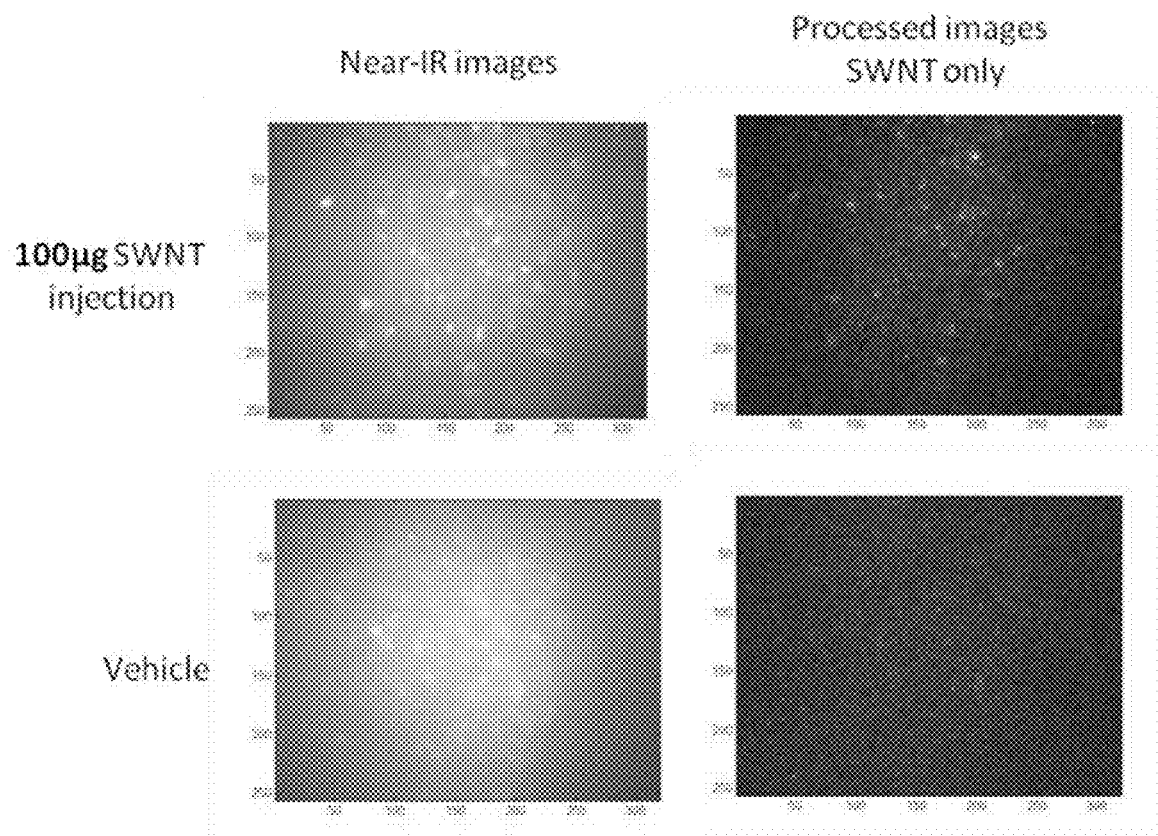
FIG. 19 shows a macroscopic image of mouse spleen 24 hrs after administration of 100 mg SWCNT in 3% PLURONIC (top) compared to mouse spleen 24 hrs after administration of a vehicle control (bottom).

After blood was collection, a necropsy was performed and the brain, heart, lung, liver, spleen, and kidneys were removed. The presence of SWCNT was visually checked for in the IP cavity and the organs collected. The organs collected (brain, heart, lung, liver, spleen, and kidneys) were then embedded in paraffin. Four micron slices from the liver and spleen from each group were made and mounted onto slides that were evaluated microscopically for the presence of SWCNT. Visual inspection showed that the organs did not exhibit abnormal attributes, and there was no change in organ weights at either 24 hr or 1 week. Microscopic examination of liver and spleen from animals sacrificed 24 hr after treatment showed that these tissues contained SWCNT. FIG. 19 shows macroscopic near-infrared (NIR) images and processed images of the spleen of a mouse dosed with 100 μg SWCNT at 24 hrs (top) compared with NIR and processed images of a mouse administered vehicle (bottom). SWCNT can be seen throughout the sample in the mouse administered 100 μg of SWCNT. Microscopic examination also indicated that there were a greater number of SWCNT in the organs of animals treated with 100 μg versus 50 μg SWCNT.

Figure 20:
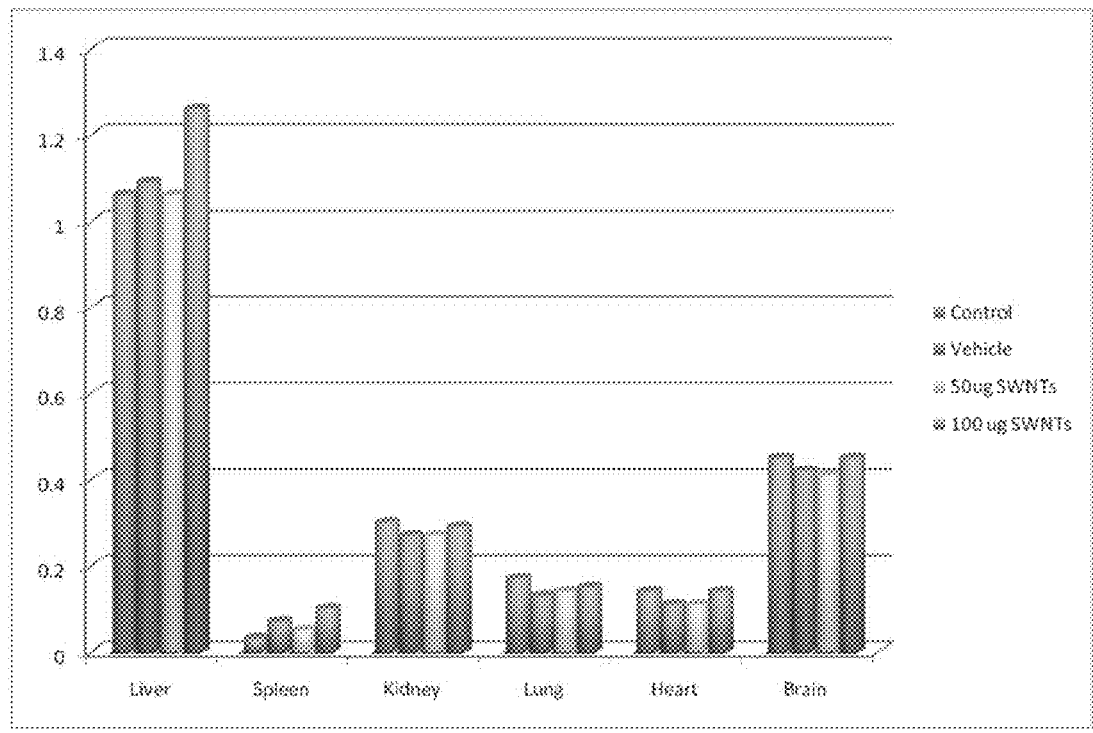
FIG. 20 shows a bar graph comparing the average weight of liver, spleen, kidney, lung, heart, and brain of control mice and mice administered a vehicle, 50 μg of SWCNT, and 100 μg of SWCNT.
Figure 21:
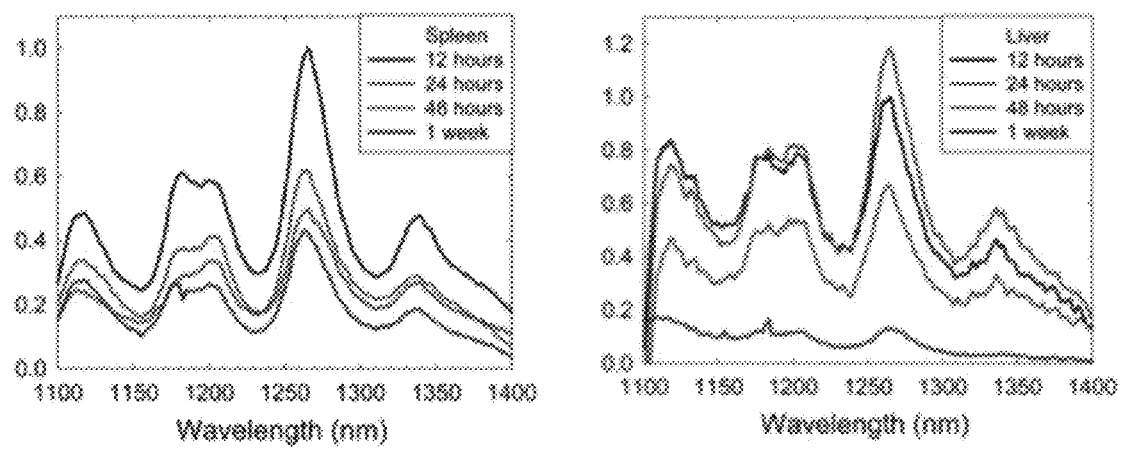
FIG. 21 shows a fluorescence spectroscopy analysis of liver and spleen 12 hours, 24 hours, 48 hours, and 1 week after intravenous administration of 100 μg of optimized SWCNT.

After sacrifice of animals treated for 1 week organs (brain, heart, lung, liver, spleen, and kidneys) were excised and weighed. As shown in FIG. 20, the weight of the brain, heart, lung, liver, spleen, and kidneys were not significantly effected by SWCNT administration. After the organs were weighed, they were placed in 4% NaDOC for 30 min at room temperature and then sonicated to breakup the tissue. Tissues and fecal samples were further homogenized for 10 second bursts for a total of 2 minutes using a tip sonicator ultrasonic processor. Tissues and feces were placed on ice in between sonication bursts and place at 4° C. The tissue and fecal suspensions were centrifuged at 40,000 RPM for 5 minutes, and the supernatant collected and placed in a clean eppendorf tube. The tissue homoganates were analyzed to quantify the SWCNT concentration using NanoSpectralyzer. These data were combined with animals treated for 12, 24 and 48 hr. The only tissues with SWCNT that could be measured were the liver and spleen, and the results are provided in FIG. 21.

A second pharmacokinetic study was undertaken to evaluate a single i.v. dose of 100 μg SWCNT in 6 mice at 12, 24 and 48 hrs. Six (6) 7-week old C57B16 mice were administered 100 μg SWCNT in a 3% (w/v) pluronic solution (250 mg/mL). The administration was made via 2 sequential injections into separate tail veins. Four animals were placed in metabolic cages and their urine and feces were collected at 24 hr after treatment. Two animals in the metabolic cage were sacrificed at 24 and 48 hr after treatment. Two other animals were caged separately and sacrificed at 12 hr. Following sacrifice blood and tissues were collected as per the 1 week group above. Tissues were macroscopically examined and homogenized. Homogenization was carried out as follows: brain, liver, spleen, and feces samples from these animals were placed in 1.5 mL, 0.5 mL, and 2.5 mL 4% NaDOC, respectively, for 30 min at room temperature and were then sonicated to breakup the tissue. Tissues and feces were then homogenized for 10 second bursts for a total of 2 minutes using a tip sonicator ultrasonic processor. Samples were placed on ice in between sonication bursts and stored at 4° C. The resulting solutions were analyzed for SWCNT content.

The concentration of SWCNT in tissue from animals sacrificed at 12 hr, 24 hr, 48 hr and 1 week were analyzed via fluorescence spectroscopy. Measurable levels of SWCNT were found in liver and spleen following the single i.v. dose of SWCNT solubilized in pluronic (see FIG. 21), with dose-dependent tissue levels in each organ. The SWCNT were rapidly eliminated from each organ over a 1 week period. A few loci of SWCNT deposits were observed on the surface of the liver (100 μg) at 24 hr but not at 1 wk. None were observed on the surface of the spleen. No other tissue evaluated showed any SWCNT content at these time points, and no SWCNT could be identified in the urine and feces collected from animals placed in the metabolic chamber at any time point. No SWCNT could be measured in brain, urine, or feces by this methodology.

Figure 22:
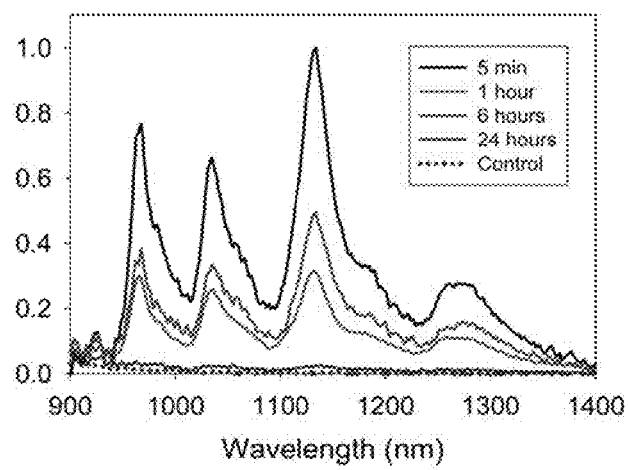
FIG. 22 shows a fluorescence spectroscopy analysis of the plasma SWCNT content 5 min, 1 hour, 6 hours, and 24 hours after administration of 100 μg of optimized SWCNT (FIG. 22A), and the average SWCNT content based on FIG. 22A plotted over time (FIG. 22B).
Figure 22:
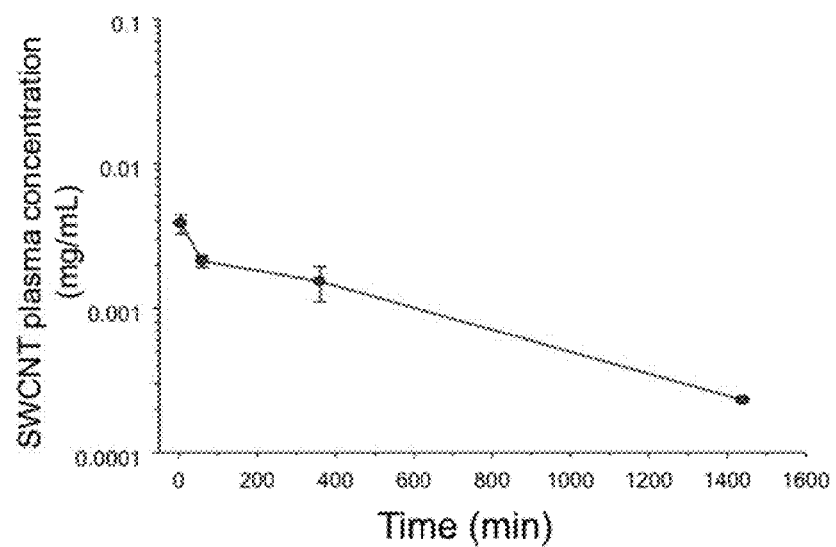

A pharmacokinetic study was performed on a group of 8 mice, each receiving an bolus i.v. injection dose 100 μg SWCNT in 3 w/v % pluronic. Blood samples were taken, 2 mice per time point (2 time points per mouse) at 5 min, 1 hr, 6 hr, and 24 hr. Blood plasma (50 μl) was diluted in 300 μl of 2% NaDOC. The plasma SWCNT content was measured by fluorescence spectroscopy (FIG. 22A). The concentration of SWCNT was calculated for each spectra and the average for each time point was plotted versus time (FIG. 22B). PK demonstrated first order elimination kinetics and was calculated from the terminal slope ($t_{1/2\ elim}$) to be 8.2 hr. In addition, pluronic solubilized SWCNT were readily eliminated from the circulation over a 24 hr time period and from the liver and spleen over a 1 week period.

A similar pharmacokinetic study was performed with SWCNT solubilized siRNA in 0.9% NaCl. C57B16 mice were administered 150 μL solution containing 4.5 μg of SWCNT/siRNA. Blood and organs were collected at 2 min, 5 min, 15 min, 30 min, 45 min, 6 hr, and 24 hr. No SWCNT were detected in any blood sample probably due to the low dose administered.

Example 8

In vivo Knockdown of Thioredoxin

Systemically delivered SWCNT/siRNA complexes can produce target knockdown in organ tissue in mice. Six (6) week old C57B16 mice were administered a single i.v. dose (300 μl) of SWCNT/(Trx)siRNA in aqueous PEG 5000 (57.8 μM siRNA:446 μM PEG), in the following groups:

Grp 1.—Control: untreated
Grp 2.—Control: vehicle treated single IV dose vehicle (siRNA/PEG aqueous)
Grp 3.—SWCT treated: single IV dose PEG solubilized SWCNT/(Trx)siRNA solution: 34 μg SWCNT
Grp 4.—SWCT treated: single IV dose PEG solubilized SWCNT/(Trx)siRNA solution: 67 μg SWCNT Following SWCNT or vehicle administration animals were sacrificed at 2 mins, 15 min, 30 min, 1 hr, 4 hr, and 24 hr (two animals were sacrificed per time point), and blood and tissue samples were collected for analyses of SWCNT concentration and target inhibition. Animals were euthanized in $CO_2$, and blood was drawn by cardiac puncture and a portion was placed into a tube for (i) hematology tests including complete CBC and white blood cell differential count, (ii) blood chemistry tests including tests for kidney function using creatinine and blood urea nitrogen (BUN) and liver function using aspartate aminotransferase (AST or SGOT) and alanine aminotransferase (ALT or SGPT), and (iii) SWCNT concentration using NanoSpectralizer.

Figure 23:
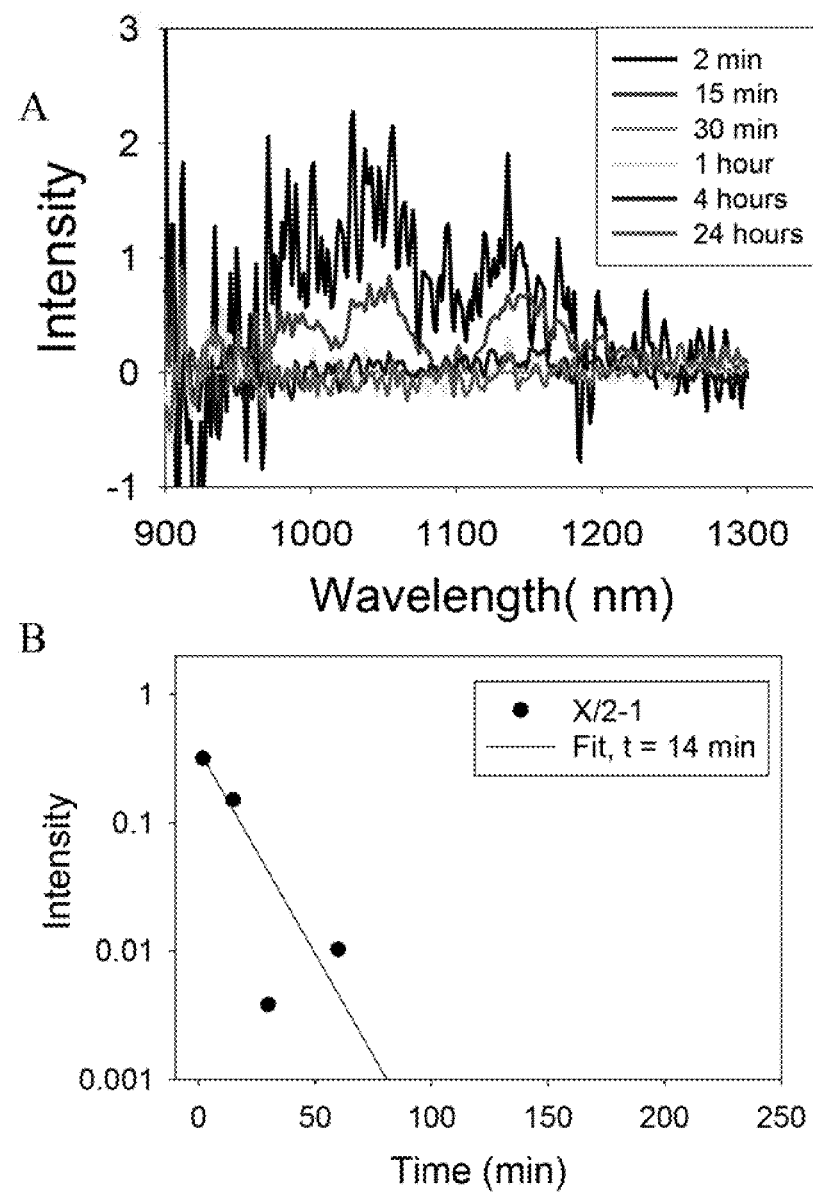
FIG. 23 shows the fluorometric analysis of SWCNT/(Trx)siRNA in the blood of mice sacrificed at 2 min, 15 min, 30 min, 1 hr, 4 hr, and 24 hr after administration of 34 μg of SWCNT/(Trx)siRNA/PEG (FIG. 23A), and a scatter plot fit to a line of the peak intensity from FIG. 23A versus time (FIG. 23B).
Figure 24:
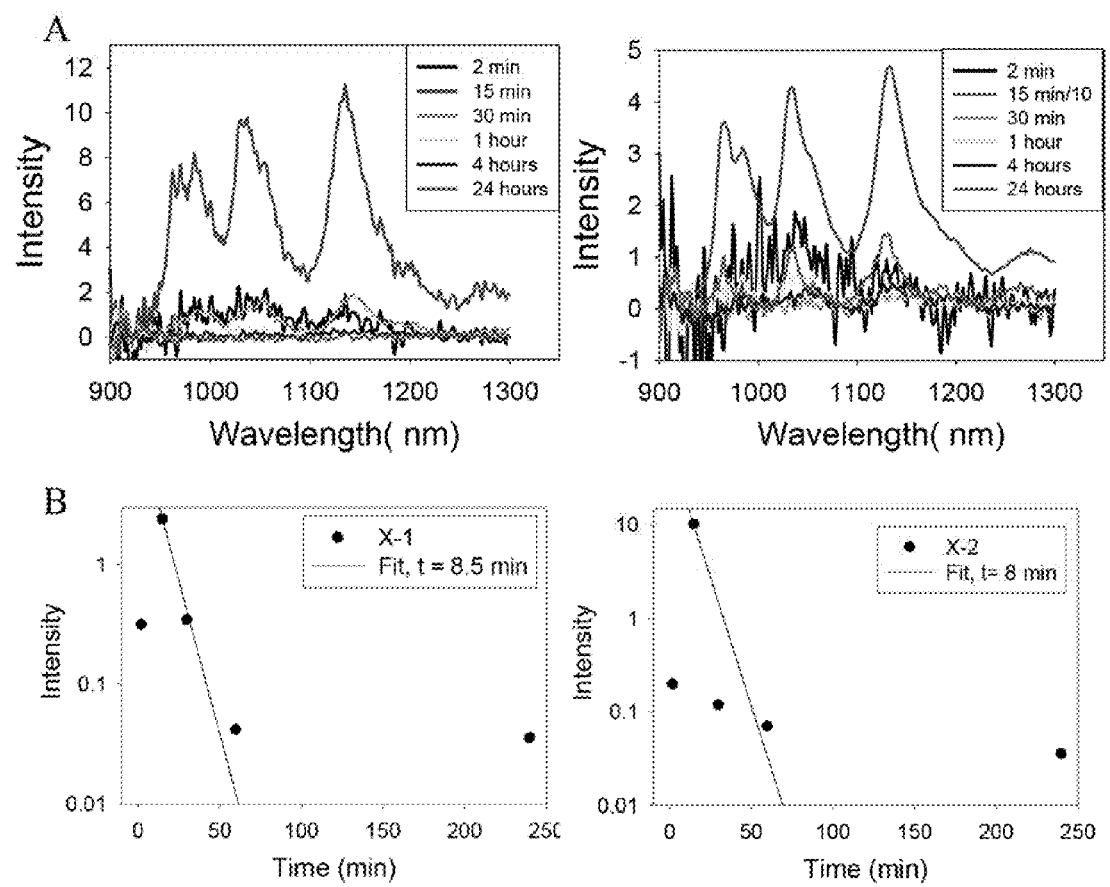
FIG. 24 shows the fluorometric analysis of SWCNT/(Trx)siRNA in the blood of mice sacrificed at 2 min, 15 min, 30 min, 1 hr, 4 hr, and 24 hr after administration of 67 μg of SWCNT/(Trx)siRNA/PEG (FIG. 24A), and a scatter plot fit to a line of the peak intensity from FIG. 24A versus time (FIG. 24B).

Blood obtained from Group 3 mice (34 μg SWCNT/(Trx) siRNA) sacrificed at the various time points were tested for SWCNT/(Trx)siRNA using a NanoSpectralizer (FIG. 23A). A scatter plot of the peak intensity over time was prepared and these data were fit to a line. As shown in FIG. 23B the slope of the line provides the half-life of the SWCNT/(Trx)siRNA complexes in circulation, which was determined to be 14 minutes based on these data. Similar SWCNT/(Trx)siRNA concentrations were determined for Group 4 mice (67 μg SWCNT/(Trx)siRNA) as shown in FIG. 24A, and these data were plotted and fit to a line (FIG. 24B). These data show a half-life for SWCNT/(Trx)siRNA in circulation of 8 minutes and 8.5 minutes. Based on this study, SWCNT/siRNA complexes are expected to have a half-life of about 8 min to about 15 min in circulation.

Figure 25:
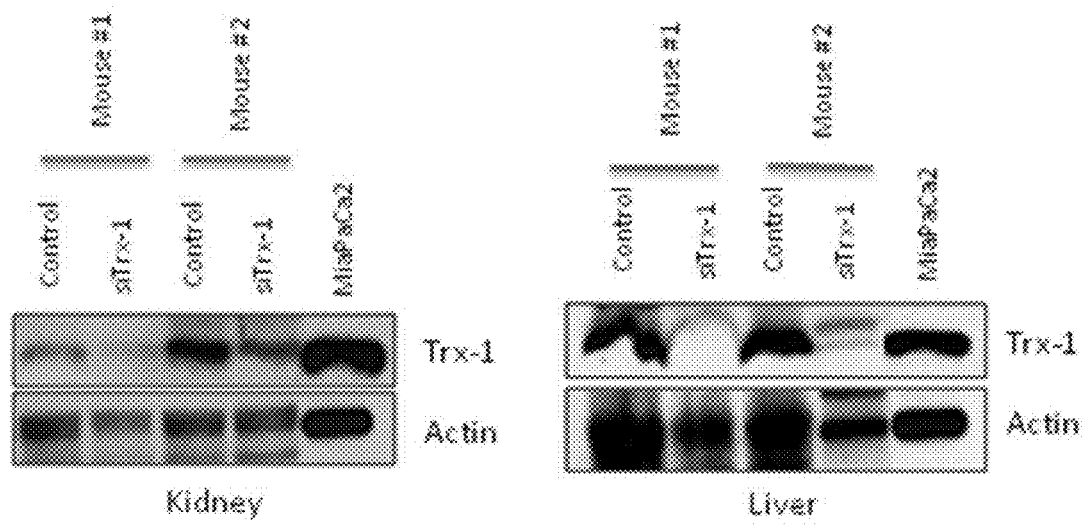
FIG. 25 shows a Western blot for thioredoxin and actin from the liver and kidney of two mice administered 67 μg of SWCNT/(Trx)siRNA.

Once the blood was collected, a necropsy was performed and the brain, heart, lung, liver, spleen, and kidneys removed. The presence of SWCNT was visually checked for in the IP cavity and the organs collected, and after the macroscopic observation, the organs were collected (brain, heart, lung, liver, spleen, and kidneys) and half of each when possible was embedded in paraffin. Slices (4 μm) from the liver and spleen from each group were made and mounted onto slides. The slides were prepared for evaluation microscopically as described above for the presence of SWCNT. Organs (liver and kidney) were homogenized and the homogenate was evaluated for Trx levels by Western Blotting. FIG. 25 shows a Western blot for Trx of the liver and kidney of two animals, M1 and M2, that were sacrificed 24 hrs after administration of SWCNT/(Trx)siRNA. These data show that SWCNT/(Trx) siRNA (x) effectively reduced thioredoxin expression in both the kidney and liver when compared to controls (c) 24 hr after SWCNT/siRNA complex administration.

Figure 26:
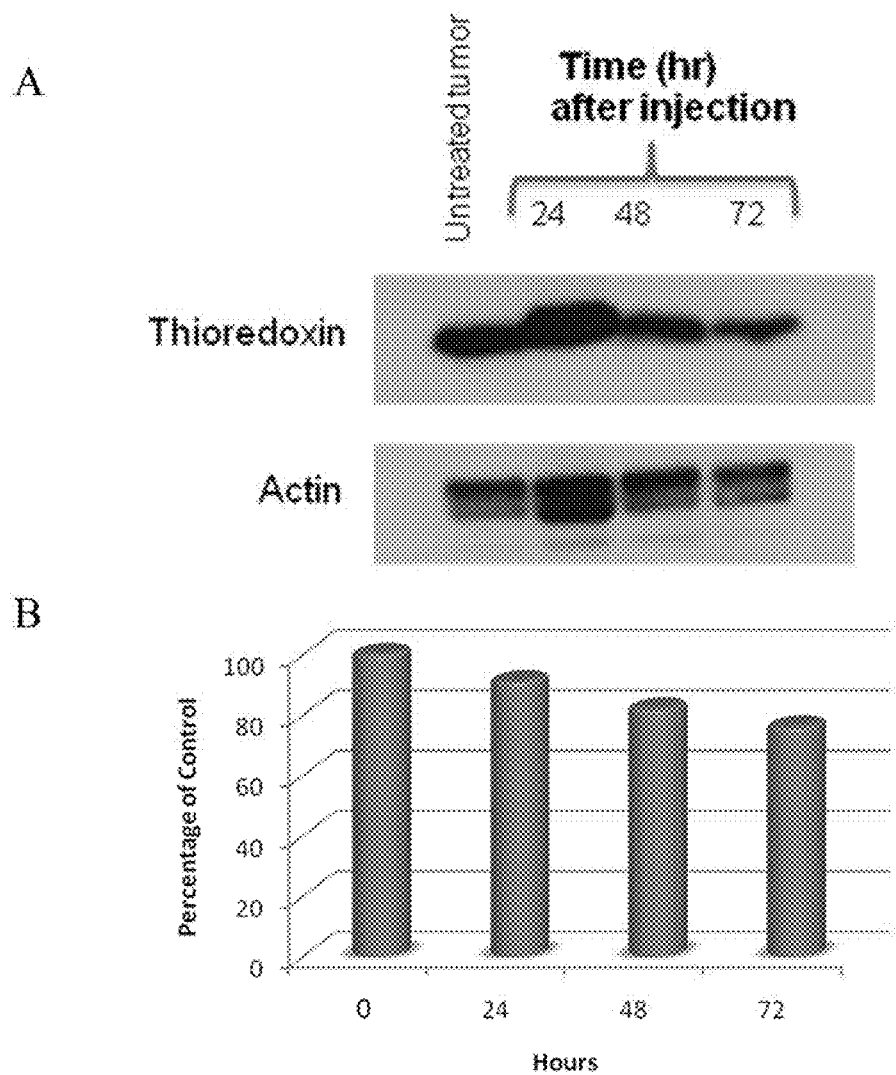
FIG. 26 shows a Western blot for thioredoxin and actin from MiaPaCa human pancreatic tumors excised from nude mice 24 hr, 48 hr, and 72 hr after administration of 39 μg of SWCNT/(Trx)siRNA (FIG. 26A).

SWCNT/(Trx)siRNA was administered to nude mice with subcutaneous MiaPaCa human pancreatic xenografts. The SWCNT complex was prepared in a solution of 100 µM siRNA and 13 µM PEG 5000 (7.7:1 molar ratio) providing a solution containing 130 mg/L of SWCNT/(Trx)siRNA. Mice were administered 39 µg total dose of SWCNT via i.v. tail vein injection. The mice were sacrificed at 24, 28, and 72 hrs (one animal per time point) after administration, organs and tumors were excised, and tumors were evaluated for Trx protein level by Western Blotting (FIG. 26A). FIG. 26B shows a bar graph indicating that Trx protein levels were reduced in a time dependent manner following a single i.v. administration of SWCNT/(Trx)siRNA.

Figure 27:
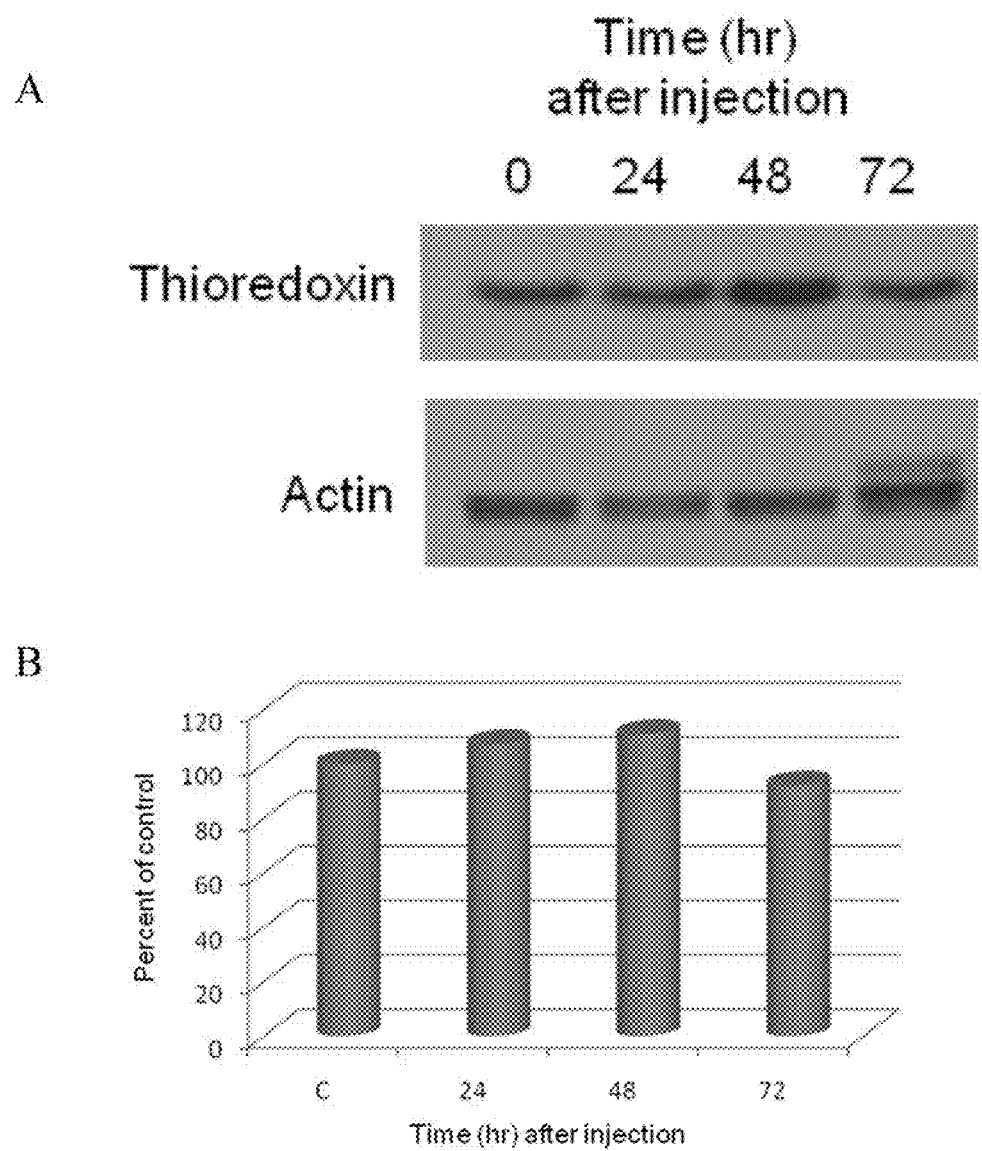
FIG. 27 shows a Western blot for thioredoxin and actin from MiaPaCa human pancreatic tumors excised from nude mice 24 hr, 48 hr, and 72 hr after administration of 94 μg of SWCNT/(Trx)siRNA (FIG. 27A).

In a second in vivo study in tumored animals, SWCNT/(Trx)siRNA was administered to nude mice with subcutaneous MiaPaCa human pancreatic xenografts with a transfected empty vector or luciferase reporter. The SWCNT complex was prepared in a solution of 100 µM siRNA and 100 µM PEG 5000 µM (1:1 molar ratio) providing a solution containing 314 mg/L SWCNT/(Trx)siRNA. Mice were administered 94 µg total dose of SWCNT via i.v. tail vein injection. The mice were sacrificed at 24, 28, and 72 hrs (one animal per time point) after administration, organs and tumors were excised, and tumor evaluated for Trx protein level by Western Blotting (FIG. 27A). FIG. 27B shows the Trx levels were reduced at 72 hrs following a single i.v. administration of SWCNT/(Trx) siRNA.

Example 9

In vivo Knockdown of EGFR and KRAS

Raw HiPco SWCNTs (Lot HPR 188.4), approximately 4.0 mg, were dispersed in 3.5 mL siRNA stock solutions (571.43 ug/mL) of either siEGFR (sequence: 5'-GUCUCUUG-GAUAUUCUCGA[dT][dT]-3' (SEQ ID 14)), siKRAS (sequence: 5'-GAGGAAAUAUGUACUACGA[dT][dT]-3' (SEQ ID 15)), or a combination of both siEGFR and siKRAS. These mixtures were tip sonicated for a total of 4 minutes in 15 second bursts at RT with 45 seconds on ice between sonication (sixteen cycles of sonication). PL-PEG (14:0 (1,2-dimyristoyl-sn-glycero-3-phosphoethanolamine-N-[methoxy(polyethylene glycol)-5000] (ammonium salt)) stock solution (10 mg/mL in DMSO) was added to SWCNT/siRNA mixture to provide a final PL-PEG solution of 8 µM. The mixture was tip sonicated for another 2 minutes in 15 seconds in bursts as described above.

Following sonication the solutions were centrifuged for 10 min at 14,000 rpm and 4° C. Supernatant containing SWCNT/siRNA solution was removed and transferred to a sterile 15 mL conical tubes and stored refrigerated at 4° C. A 200 µL sample of each solution was analyzed using NS2 Nanspectralyzer to determine SWCNT concentration.

Eight-week-old Nu/Nu female mice were inoculated subcutaneously with MiaPaCa human carcinoma cells $1 \times 10^7$ in the flank. Tumor growth was measured twice weekly and volumes determined. When tumors reached 100 mm$^3$ they were randomized into groups of 10 and administered test solutions as per study arms below through tail vein i.v. injections once per week for a total of 4 weeks. After the 4$^{th}$ injection, animals (2 per group) were sacrificed by $CO_2$ euthanasia at 24, 48, 72, 96 hours post injection. Blood samples were collected by cardiac puncture and tissues were harvested for PD and SWCNT analyses including tumor, liver, spleen, heart, kidneys, lungs, brain, muscle, and bone.

Figure 28:
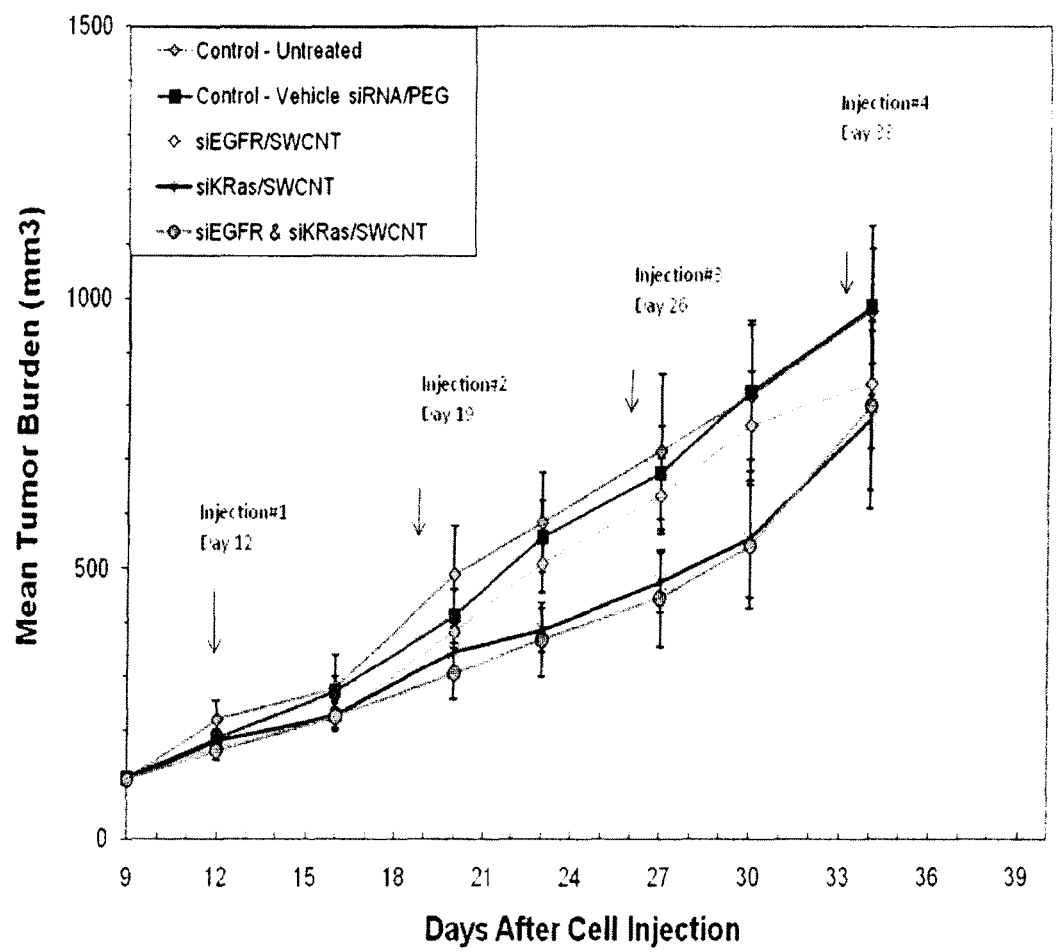
FIG. 28 shows the growth rate of tumors in animals treated with SWCNT/siEGFR, SWCNT/siKRAS, and SWCNT/siEGFR/siKRAS compared to untreated animals and vehicle controls where SWCNT/siRNA administration began 12 days after the initial injection of MiaPaCa-2 cells.

Solutions of siRNA targeting EGFR, KRAS or both complexed to SWCNT (35 µg SWCNT/dose; ~0.8 mg/kg siRNA in 0.9% saline/PL-PEG) were injected weekly via tail vein of mice bearing MiaPaCa human pancreatic tumors (groups of 8 mice). Vehicle control contained siRNA to EGFR and KRAS in 0.9% saline/PEG (1 mg/kg/dose). The initial injection of MiaPaCa cells occurred 12 days before the initial SWCNT/siRNA injections. Tumor volumes were measured twice weekly. Hematology and blood chemistry performed 24 hrs after last treatment in weekly study showed no differences in treatment group versus non-treated controls. Body weights did not change (see, FIG. 29B). As illustrated in FIG. 28, growth rate of tumors in animals treated with SWCNT/siKRAS and SWCNT/siEGFR/siKRAS were significantly less than the control vehicle between days 16 and 23.

Figure 29A:
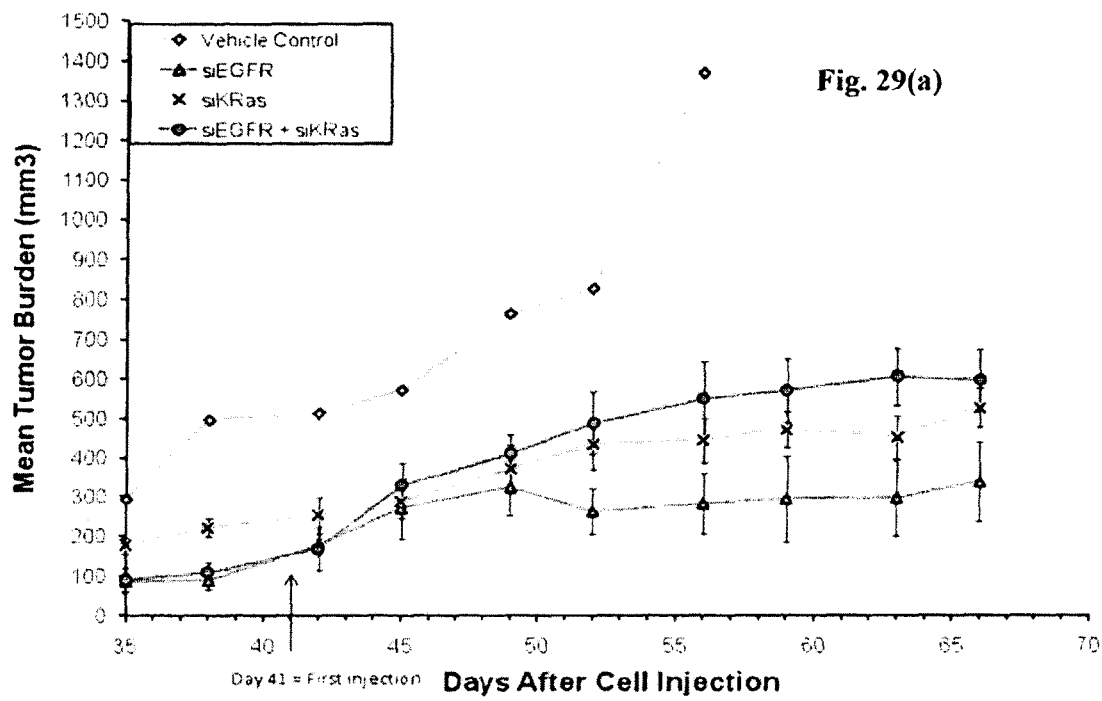
FIG. 29 shows the growth rate of tumors in animals treated with SWCNT/siEGFR, SWCNT/siKRAS, and SWCNT/siEGFR/siKRAS compared to untreated animals and vehicle controls where SWCNT/siRNA administration began 41 days after the initial injection of MiaPaCa-2 cells (FIG. 29A).
FIG. 29B shows the change in body weight of the animals over the same period.
Figure 29B:
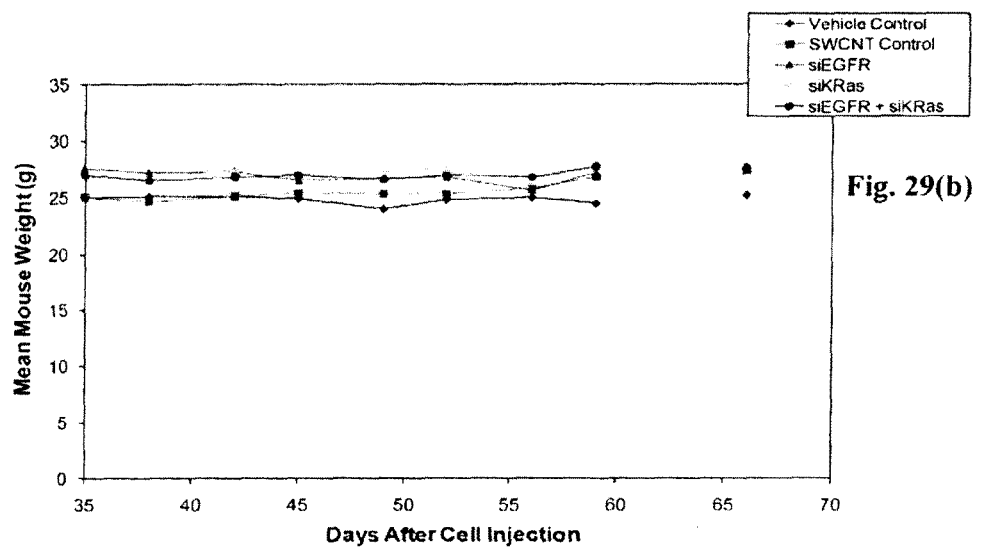

In a similar experiment, siRNA targeting EGFR, KRAS or both complexed to SWCNT were injected via tail vein of mice bearing MiaPaCa human pancreatic tumors; the cells of which were injected into the mice 41 days prior to the first SWCNT/siRNA injection twice weekly for 4 weeks. The total SWCNT load per dose was 35 µg and siRNA delivery per dose was 10 to 18 µg (0.8 mg/kg). Vehicle control contained siRNA to EGFR and KRAS in 0.9% saline/PEG (1 mg/kg/dose). Tumors and body weight were measured twice weekly. No loss in body weight was observed (FIG. 29B). As illustrated in FIG. 29A, growth rate of tumors in animals treated with SWCNT/siEGFR, SWCNT/siKRAS, and SWCNT/siEGFR/siKRAS were significantly less than the control vehicle.

Figure 30:
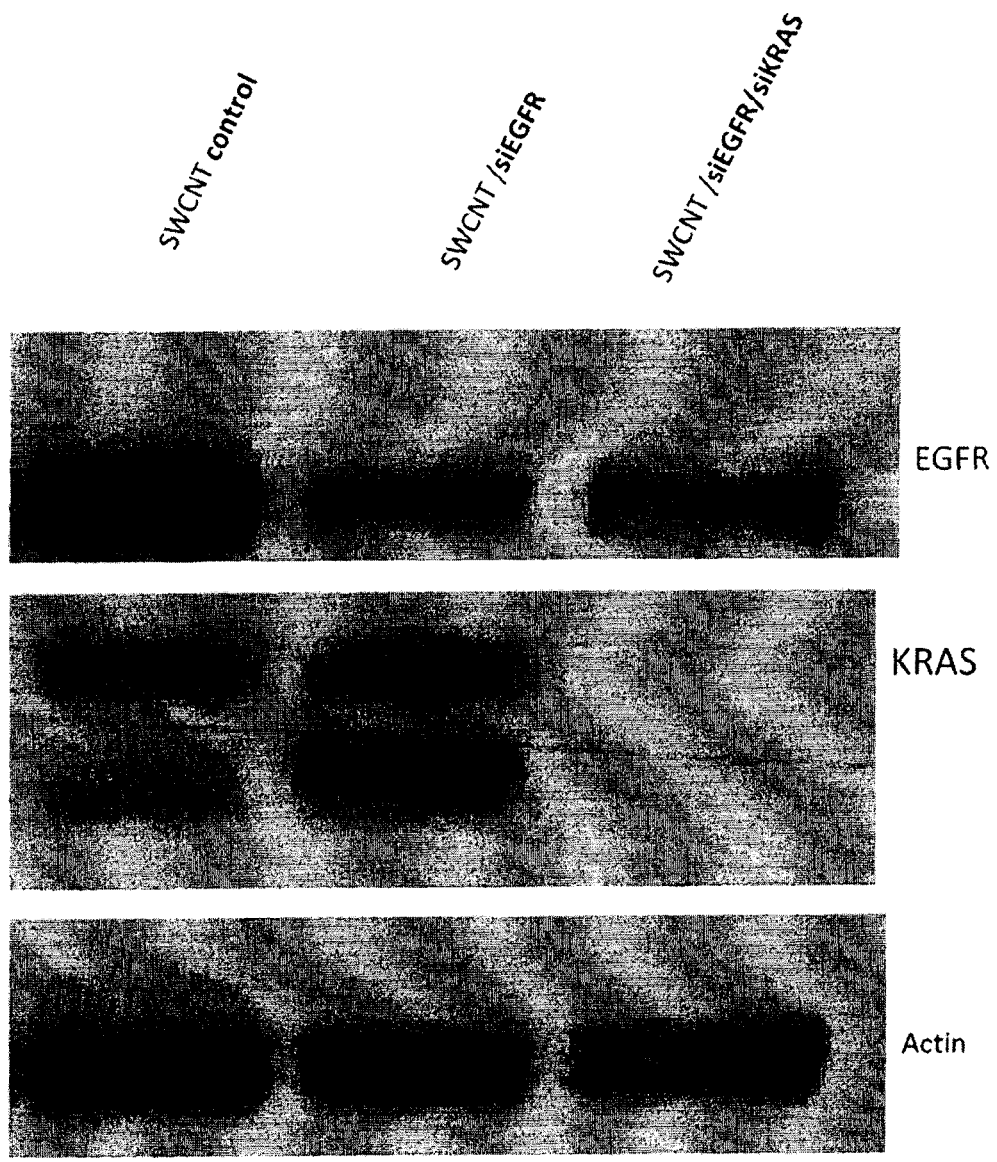
FIG. 30 shows a Western blotted for EGFR and KRAS 96 hrs following 4th treatment of mice bearing MiaPaCa-2 tumors that had been treated weekly with 35 µg SWCNT/siEGFR, SWCNT/siKRAS, or SWCNT/siEGFR/siKRAS

FIG. 30 shows a Western blotted for EGFR and KRAS 96 hrs following 4th treatment of mice bearing MiaPaCa-2 tumors that had been treated weekly with 35 µg SWCNT/siEGFR, SWCNT/siKRAS, or SWCNT/siEGFR/siKRAS (10 to 18 µg siRNA). As indicated, systemic delivery produced knockdown of both protein targets, EGFR and KRAS, in these human pancreatic tumor xenografts. In particular, EGFR was lowered in tumors of animals administered SWCNT/siEGFR complexes and both EGFR and KRAS in tumors of animals administered SWCNT/siEGFR/siKRAS.

What is claimed is:

1. A method for delivering siRNA to tumorigenic tissue comprising:
administering via intravenous injection to a subject having tumorigenic tissue an effective amount of a pharmaceutical composition comprising
one or more short-interfering ribonucleic acid (siRNA) complexed to single-walled carbon nanotubes; and
a pharmaceutically acceptable excipient;
administering one or more subsequent doses of the pharmaceutical composition about every 12 to 24 hours based on effect without regard to blood plasma concentration levels of the short-interfering ribonucleic acid (siRNA) complexed to single-walled carbon nanotubes.

2. The method of claim 1, wherein the subject is selected from a mammal, a mouse, and a human.

3. The method of claim 1, wherein the subject is a human having cancer.

4. The method of claim 1, wherein the effective amount comprises up to about 100 mg of the one or more short-interfering ribonucleic acid (siRNA) complexed to single-walled carbon nanotubes.

5. The method of claim 1, wherein the effective amount comprises up to about 30 mg of the one or more short-interfering ribonucleic acid (siRNA) complexed to single-walled carbon nanotubes.

6. The method of claim 1, wherein the effective amount comprises from about 15 mg to about 100 mg of the one or more short-interfering ribonucleic acid (siRNA) complexed to single-walled carbon nanotubes.

7. The method of claim 1, wherein the effective amount comprises from about 15 mg to about 30 mg of the one or more short-interfering ribonucleic acid (siRNA) complexed to single-walled carbon nanotubes.

8. The method of claim 1, wherein a substantial portion of the one or more short-interfering ribonucleic acid (siRNA) complexed to single-walled carbon nanotubes accumulates in the tumorigenic tissue at sufficient concentrations to inhibit expression of at least one target associated with the one or more short-interfering ribonucleic acid (siRNA)tissue within about 1 hour after administration.

9. The method of claim 1, wherein substantially none of the one or more short-interfering ribonucleic acid (siRNA) complexed to single-walled carbon nanotubes are in circulation from about 5 to about 15 minutes after administration of the one or more short-interfering ribonucleic acid (siRNA) complexed to single-walled carbon nanotubes.

10. The method of claim 1, wherein the effective amount of one or more short-interfering ribonucleic acid (siRNA) is non-covalently complexed to single-walled carbon nanotubes.

11. A method for inhibiting expression of a gene in a subject comprising:
administering to the subject an effective amount of a pharmaceutical composition comprising:
an effective amount of one or more short-interfering ribonucleic acid (siRNA) complexed to single-walled carbon nanotubes; and
a pharmaceutically acceptable excipient;
and administering one or more subsequent doses of the pharmaceutical composition about every 12 to 24 hours based on effect without regard to blood plasma concentration levels of the short-interfering ribonucleic acid (siRNA) complexed to single-walled carbon nanotubes.

12. A method for delivering siRNA to tumorigenic tissue comprising:
administering via intravenous injection to a subject having tumorigenic tissue a pharmaceutical composition comprising:
an effective amount of one or more short-interfering ribonucleic acid (siRNA) complexed to carbon nanotubes; and
a pharmaceutically acceptable excipient.

* * * * *

SEQUENCE LISTING

<160> NUMBER OF SEQ ID NOS: 15

<210> SEQ ID NO 1
<211> LENGTH: 19
<212> TYPE: RNA
<213> ORGANISM: Artificial Sequence
<220> FEATURE:
<223> OTHER INFORMATION: Synthesized

```
<400> SEQUENCE: 1
ccugugucua aaucugaac                                                    19

<210> SEQ ID NO 2
<211> LENGTH: 20
<212> TYPE: RNA
<213> ORGANISM: Artificial Sequence
<220> FEATURE:
<223> OTHER INFORMATION: Synthesized

<400> SEQUENCE: 2
cuaccuucgu gauucuguuu                                                   20

<210> SEQ ID NO 3
<211> LENGTH: 19
<212> TYPE: RNA
<213> ORGANISM: Artificial Sequence
<220> FEATURE:
<223> OTHER INFORMATION: Synthesized

<400> SEQUENCE: 3
gcacaauaga cagcgaaac                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthesized

<400> SEQUENCE: 4
cuacuuucuu aauggcuua                                                    19

<210> SEQ ID NO 5
<211> LENGTH: 22
<212> TYPE: RNA
<213> ORGANISM: Artificial Sequence
<220> FEATURE:
<223> OTHER INFORMATION: Synthesized

<400> SEQUENCE: 5
caaccaaagu cgaauauuga uu                                                22

<210> SEQ ID NO 6
<211> LENGTH: 21
<212> TYPE: RNA
<213> ORGANISM: Artificial Sequence
<220> FEATURE:
<223> OTHER INFORMATION: Synthesized

<400> SEQUENCE: 6
caagaagaau gaauacaguu u                                                 21

<210> SEQ ID NO 7
<211> LENGTH: 21
<212> TYPE: RNA
<213> ORGANISM: Artificial Sequence
<220> FEATURE:
<223> OTHER INFORMATION: Synthesized

<400> SEQUENCE: 7
gaagaugucc auggaaauau u                                                 21

<210> SEQ ID NO 8
```

```
<211> LENGTH: 21
<212> TYPE: RNA
<213> ORGANISM: Artificial Sequence
<220> FEATURE:
<223> OTHER INFORMATION: Synthesized

<400> SEQUENCE: 8
caacacgccu cauccucuau u                                              21

<210> SEQ ID NO 9
<211> LENGTH: 19
<212> TYPE: RNA
<213> ORGANISM: Artificial Sequence
<220> FEATURE:
<223> OTHER INFORMATION: Synthesized

<400> SEQUENCE: 9
cgucuuuaga uuccuauau                                                 19

<210> SEQ ID NO 10
<211> LENGTH: 19
<212> TYPE: RNA
<213> ORGANISM: Artificial Sequence
<220> FEATURE:
<223> OTHER INFORMATION: Synthesized

<400> SEQUENCE: 10
guuguuccua cuucagaua                                                 19

<210> SEQ ID NO 11
<211> LENGTH: 17
<212> TYPE: RNA
<213> ORGANISM: Artificial Sequence
<220> FEATURE:
<223> OTHER INFORMATION: Synthesized

<400> SEQUENCE: 11
gucgucuuua gauuccu                                                   17

<210> SEQ ID NO 12
<211> LENGTH: 19
<212> TYPE: RNA
<213> ORGANISM: Artificial Sequence
<220> FEATURE:
<223> OTHER INFORMATION: Synthesized

<400> SEQUENCE: 12
gaucuaccga aagagucau                                                 19

<210> SEQ ID NO 13
<211> LENGTH: 19
<212> TYPE: RNA
<213> ORGANISM: Artificial Sequence
<220> FEATURE:
<223> OTHER INFORMATION: Synthesized

<400> SEQUENCE: 13
uagcgacauu uguguaguu                                                 19

<210> SEQ ID NO 14
<211> LENGTH: 20
<212> TYPE: DNA
<213> ORGANISM: Artificial Sequence
<220> FEATURE:
<223> OTHER INFORMATION: Synthesized

<400> SEQUENCE: 14
```

```
gucucuugga uauucucgat                                             20

<210> SEQ ID NO 15
<211> LENGTH: 21
<212> TYPE: DNA
<213> ORGANISM: Artificial Sequence
<220> FEATURE:
<223> OTHER INFORMATION: Synthesized

<400> SEQUENCE: 15
gaggaaauau guacuacgat t                                           21
```